(12) United States Patent
Mirkin et al.

(10) Patent No.: US 11,883,535 B2
(45) Date of Patent: *Jan. 30, 2024

(54) LIPOSOMAL PARTICLES, METHODS OF MAKING SAME AND USES THEREOF

(71) Applicants: NORTHWESTERN UNIVERSITY, Evanston, IL (US); EXICURE, INC., Skokie, IL (US)

(72) Inventors: Chad A. Mirkin, Wilmette, IL (US); Sonbinh T. Nguyen, Evanston, IL (US); Resham Singh Banga, Chicago, IL (US); Natalia Chernyak, Evanston, IL (US); Sergei Gryaznov, San Mateo, CA (US); Aleksandar Radovic-Moreno, Evanston, IL (US); Christopher Mader, Cambridge, MA (US)

(73) Assignees: NORTHWESTERN UNIVERSITY, Evanston, IL (US); EXICURE, INC., Skokie, IL (US)

( * ) Notice: Subject to any disclaimer, the term of this patent is extended or adjusted under 35 U.S.C. 154(b) by 717 days.

This patent is subject to a terminal disclaimer.

(21) Appl. No.: 17/011,658

(22) Filed: Sep. 3, 2020

(65) Prior Publication Data

US 2021/0052497 A1 Feb. 25, 2021

Related U.S. Application Data

(63) Continuation of application No. 16/242,704, filed on Jan. 8, 2019, now Pat. No. 10,792,251, which is a continuation of application No. 15/101,523, filed as application No. PCT/US2014/068429 on Dec. 3, 2014, now Pat. No. 10,182,988.

(60) Provisional application No. 61/982,269, filed on Apr. 21, 2014, provisional application No. 61/911,334, filed on Dec. 3, 2013.

(51) Int. Cl.
*A61K 9/127* (2006.01)
*A61K 48/00* (2006.01)
*C12N 15/11* (2006.01)
*C12N 15/113* (2010.01)

(52) U.S. Cl.
CPC ............ *A61K 9/1271* (2013.01); *A61K 9/127* (2013.01); *A61K 9/1277* (2013.01); *A61K 48/00* (2013.01); *C12N 15/111* (2013.01); *C12N 15/113* (2013.01); *C12N 2310/11* (2013.01); *C12N 2310/12* (2013.01); *C12N 2310/14* (2013.01); *C12N 2310/141* (2013.01); *C12N 2320/32* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,469,863 A | 9/1984 | Ts'o et al. |
| 4,476,301 A | 10/1984 | Imbach et al. |
| 4,845,205 A | 7/1989 | Huynh Dinh et al. |
| 4,981,957 A | 1/1991 | Lebleu et al. |
| 5,008,050 A | 4/1991 | Cullis et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,134,066 A | 7/1992 | Rogers et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,194,599 A | 3/1993 | Froehler et al. |

(Continued)

FOREIGN PATENT DOCUMENTS

| | | |
|---|---|---|
| CN | 101180400 A | 5/2008 |
| CN | 103212089 A | 7/2013 |

(Continued)

OTHER PUBLICATIONS

Watts, et al. (2012) "Silencing disease genes in the laboratory and the clinic", Journal of Pathology, 226: 365-79. (Year: 2012).*
Samadikhah, et al. (2011) "Preparation, characterization, and efficient transfection of cationic liposomes and nanomagnetic cationic liposomes", International Journal of Nanomedicine, 6: 2275-83. (Year: 2011).*
Raouane, et al. (2012) "Lipid Conjugated Oligonucleotides: A Useful Strategy for Delivery", Bioconjugate Chemistry, 23: 1091-1104. (Year: 2012).*
Agbasi-Porter et al., Transcription inhibition using oligonucleotide-modified gold nanoparticles, Bioconjugate Chem., 17(5):1178-83 (2006).

(Continued)

*Primary Examiner* — Robert M Kelly
(74) *Attorney, Agent, or Firm* — MARSHALL, GERSTEIN & BORUN LLP

(57) ABSTRACT

Liposomes termed as small unilamellar vesicles (SUVs), can be synthesized in the 20-50 nm size range, but encounter challenges such as instability and aggregation leading to inter-particle fusion. This limits their use as a therapeutic delivery agent. Increasing the surface negative charge of SUVs, via the attachment of anionic entities such as DNA/RNA, increases the colloidal stability of these vesicles. Additionally, the dense spherical arrangement and radial orientation of nucleic acids exhibits unique chemical and biological properties, unlike their linear counterparts. These liposomal particles, are non-toxic and though anionic, can efficiently enter cells without the aid of ancillary cationic transfection agents in a non-immunogenic fashion. These exceptional properties allow their use as delivery agents for gene regulation in different therapies and offer an alternative platform to metal core spherical nucleic acids.

23 Claims, 19 Drawing Sheets

Specification includes a Sequence Listing.

(56) References Cited

U.S. PATENT DOCUMENTS

| | | |
|---|---|---|
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,264,618 A | 11/1993 | Felgner et al. |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,367,066 A | 11/1994 | Urdea et al. |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,502,177 A | 3/1996 | Matteucci et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,555 A | 10/1996 | Froehler et al. |
| 5,567,811 A | 10/1996 | Misiura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci et al. |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,658,873 A | 8/1997 | Bertsch-Frank et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,714,331 A | 2/1998 | Buchardt et al. |
| 5,719,262 A | 2/1998 | Buchardt et al. |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,747 A | 8/1998 | Schally et al. |
| 5,814,666 A | 9/1998 | Green et al. |
| 5,830,653 A | 11/1998 | Froehler et al. |
| 5,955,589 A | 9/1999 | Cook et al. |
| 6,005,096 A | 12/1999 | Matteucci et al. |
| 6,051,698 A | 4/2000 | Janjic et al. |
| 6,239,116 B1 | 5/2001 | Krieg et al. |
| 6,271,209 B1 | 8/2001 | Smith et al. |
| 6,406,705 B1 | 6/2002 | Davis et al. |
| 6,677,153 B2 | 1/2004 | Iversen |
| 7,404,969 B2 | 7/2008 | Chen et al. |
| 7,514,099 B2 | 4/2009 | Chen et al. |
| 7,833,992 B2 | 11/2010 | Vargeese et al. |
| 7,964,578 B2 | 6/2011 | Vargeese et al. |
| 8,507,200 B2 | 8/2013 | Mirkin et al. |
| 8,846,080 B2 | 9/2014 | Biemans et al. |
| 8,933,046 B2 | 1/2015 | Machuy et al. |
| 8,940,310 B2 | 1/2015 | Barrat et al. |
| 9,364,433 B2 | 6/2016 | Andersson et al. |
| 9,693,957 B2 | 7/2017 | Lin et al. |
| 9,868,955 B2 | 1/2018 | Guiducci et al. |
| 9,901,616 B2 | 2/2018 | Dhar et al. |
| 10,182,988 B2 * | 1/2019 | Mirkin ................... A61K 9/127 |
| 10,208,310 B2 | 2/2019 | Mader et al. |
| 10,653,780 B2 | 5/2020 | Hope et al. |
| 2002/0172711 A1 | 11/2002 | Martin et al. |
| 2003/0026782 A1 | 2/2003 | Krieg |
| 2003/0044354 A1 | 3/2003 | Carpenter et al. |
| 2003/0147966 A1 | 8/2003 | Franzen et al. |
| 2003/0170162 A1 | 9/2003 | Nayfeh et al. |
| 2004/0014956 A1 | 1/2004 | Woolf et al. |
| 2004/0033197 A1 | 2/2004 | Madar et al. |
| 2004/0053384 A1 | 3/2004 | Sligar et al. |
| 2004/0158051 A1 | 8/2004 | Ozkan et al. |
| 2004/0170560 A1 | 9/2004 | Fossheim et al. |
| 2004/0219565 A1 | 11/2004 | Kauppinen et al. |
| 2005/0130167 A1 | 6/2005 | Bao et al. |
| 2005/0130911 A1 | 6/2005 | Uhlmann et al. |
| 2006/0014191 A1 | 1/2006 | Lao et al. |
| 2006/0083781 A1 | 4/2006 | Shastri et al. |
| 2006/0292174 A1 | 12/2006 | de los Rios et al. |
| 2007/0243136 A1 | 10/2007 | Fisher et al. |
| 2007/0298257 A1 | 12/2007 | Ludwig et al. |
| 2008/0175893 A1 | 7/2008 | Huang et al. |
| 2008/0181928 A1 | 7/2008 | Hakimi-Mehr et al. |
| 2008/0194463 A1 | 8/2008 | Weller et al. |
| 2008/0311182 A1 | 12/2008 | Ferrari et al. |
| 2009/0018028 A1 | 1/2009 | Lindsay et al. |
| 2009/0053169 A1 | 2/2009 | Castillo et al. |
| 2009/0322327 A1 | 12/2009 | Gao |
| 2010/0003317 A1 | 1/2010 | Akinc et al. |
| 2010/0092486 A1 | 4/2010 | Kandimalla et al. |
| 2010/0144848 A1 | 6/2010 | Vogel et al. |
| 2010/0166842 A1 | 7/2010 | Lu et al. |
| 2010/0267814 A1 | 10/2010 | Bennett et al. |
| 2011/0020242 A1 | 1/2011 | Zheng et al. |
| 2011/0052680 A1 | 3/2011 | Hendrickson et al. |
| 2011/0052697 A1 | 3/2011 | Farokhzad et al. |
| 2011/0159081 A1 | 6/2011 | Biemans et al. |
| 2011/0201594 A1 | 8/2011 | Murthi et al. |
| 2011/0223257 A1 | 9/2011 | Zhao et al. |
| 2011/0229529 A1 | 9/2011 | Irvine et al. |
| 2011/0237435 A1 | 9/2011 | Ryan |
| 2012/0082616 A1 | 4/2012 | Trawick et al. |
| 2012/0149843 A1 | 6/2012 | Chien et al. |
| 2012/0282186 A1 | 11/2012 | Mirkin et al. |
| 2013/0028857 A1 | 1/2013 | Gao et al. |
| 2013/0089614 A1 | 4/2013 | Zhang et al. |
| 2013/0123333 A1 | 5/2013 | Mirkin et al. |
| 2013/0149374 A1 | 6/2013 | Lee et al. |

(56) References Cited

U.S. PATENT DOCUMENTS

| | | | |
|---|---|---|---|
| 2013/0196951 | A1 | 8/2013 | Schoenfisch et al. |
| 2013/0252852 | A1 | 9/2013 | Pfeiffer et al. |
| 2013/0295129 | A1 | 11/2013 | Irvine et al. |
| 2013/0315831 | A1 | 11/2013 | Shi et al. |
| 2014/0065425 | A1 | 3/2014 | Bogdanov |
| 2015/0080320 | A1 | 3/2015 | Desai |
| 2015/0111790 | A1 | 4/2015 | Ategeka et al. |
| 2016/0108123 | A1 | 4/2016 | Freeman et al. |
| 2016/0186178 | A1 | 6/2016 | Radovic-Moreno et al. |
| 2016/0194642 | A1 | 7/2016 | Gryaznov et al. |
| 2016/0237429 | A1 | 8/2016 | Cubillos-Ruiz et al. |
| 2016/0274134 | A1 | 9/2016 | Mutharasan et al. |
| 2016/0310425 | A1 | 10/2016 | Mirkin et al. |
| 2017/0157048 | A1 | 6/2017 | Radovic-Moreno et al. |
| 2018/0222982 | A1 | 8/2018 | Dranoff et al. |
| 2020/0030440 | A1 | 1/2020 | Bazmorelli et al. |

FOREIGN PATENT DOCUMENTS

| | | |
|---|---|---|
| EP | 1 072 679 A2 | 1/2001 |
| EP | 2162117 A2 | 3/2010 |
| EP | 2399608 A1 | 12/2011 |
| EP | 2162117 B1 | 2/2018 |
| WO | WO-1996/034876 A1 | 11/1996 |
| WO | WO-1997/12896 A1 | 4/1997 |
| WO | WO-98/18810 A1 | 5/1998 |
| WO | WO-1998/39352 A1 | 9/1998 |
| WO | WO-1999/14226 A2 | 3/1999 |
| WO | WO-2003/086280 A2 | 10/2003 |
| WO | WO-2005/030259 A2 | 4/2005 |
| WO | WO-2005/063201 A2 | 7/2005 |
| WO | WO-2005/063288 A1 | 7/2005 |
| WO | WO-2006/099445 A2 | 9/2006 |
| WO | WO-2007008463 A2 | 1/2007 |
| WO | WO-2007/064857 A2 | 6/2007 |
| WO | WO-2007/096134 A1 | 8/2007 |
| WO | WO-2008/014979 A2 | 2/2008 |
| WO | WO-2009/061515 A1 | 5/2009 |
| WO | WO-2009/073984 A1 | 6/2009 |
| WO | WO-2009/120887 A2 | 10/2009 |
| WO | WO-2010/105209 A1 | 9/2010 |
| WO | WO-2012/055933 A1 | 5/2012 |
| WO | WO-2012/068470 A2 | 5/2012 |
| WO | WO-2013/012628 A2 | 1/2013 |
| WO | WO-2013/049941 A1 | 4/2013 |
| WO | WO-2013/151771 A1 | 10/2013 |
| WO | WO-2014/169264 A2 | 10/2014 |
| WO | WO-2015/013673 A1 | 1/2015 |
| WO | WO-2015/013675 A1 | 1/2015 |
| WO | WO-2015/187966 A1 | 12/2015 |
| WO | WO-2017/035278 A1 | 3/2017 |
| WO | WO-2018/067302 A2 | 4/2018 |

OTHER PUBLICATIONS

Alemdaroglu et al.,DNA Block Copolymer Micelles—A combinatorial Tool for Cancer Tanotechnology, Advanced Materials 20: 899 (2008).
Ali et al., "Vaccines Combined with Immune Checkpoint Antibodies Promote Cytotoxic T-cell Activity and Tumor Eradication," Cancer Immunology Research 4(2):95-100 (2016).
Altschul et al., Basic local alignment search tool, J. Mol. Biol. 215:403-10 (1990).
Andrews, et al., "Conjugation of Lipid and CpG-Containing Oligonucleotide Yields an Efficient Method for Liposome Incorporation," Bioconjugate Chem 22:1279-1286 (2011).
Bae et al., "Targeted drug delivery to tumors: myths, reality and possibility." J Control Release 153(3):198-205 (2011).
Banchelli et al., "Phospholipid membranes decorated by cholesterol-based oligonucleotides as soft hybrid nanostructures," J. Phys. Chem. B 112:10942-52 (2008).
Banga et al., "Liposomal spherical nucleic acids," J Am Chem Soc. 136(28):9866-9 (2014).

Bouderault et al., "Nanoscale tools to selectively destroy cancer cells." Chem Commun. (18):2118-20 (2008).
Briley et al., In Nanomaterials for Biomedicine; American Chemical Society, 1119:1-20 (2012).
Bunge et al., Lipophilic oligonucleotides spontaneously insert into lipid membranes, bind complementary DNA strands, and sequester into lipid-disordered domains, Langmuir, 23(8):4455-64 (2007).
Burgess, Liposome preparation—Avanti@ Polar Lipids. Sigma-Aldrich. 3 pages (1998).
Cagdas et al., "Liposomes as Potential Drug Carrier Systems for Drug Delivery," In Application of Nanotechnology in Drug Delivery, Chapter 1, 51 pages (2014).
Cao et al., Reversible Cell-Specific Drug Delivery with Aptamer-Functionalized Liposomes, Angew. Chem. Int. Ed., 48:6494-8 (2009).
Capaccioli et al., "Cationic lipids improve antisense oligonucleotide uptake and prevent degradation in cultured cells and inhuman serum," Biochem. Biophys. Res. Commun. 197(2):818-25 (1993).
Chien et al., DNA-nanoparticle micelles as supramolecular fluorogenic substrates enabling catalytic signal amplification and detection by DNAzyme probes, Chem. Commun., 47: 167 (2011).
Chinnathambi et al,. "Binding Mode of CpG Oligodeoxynucleotides to Nanoparticles Regulates Bifurcated Cytokine induction via Toll-like Receptor 9," Scientific Reports 2:534, pp. 1-9 (2012).
Cho et al., "Targeted delivery of siRNA-generating DNA nanocassettes using multifunctional nanoparticles," Small 9(11):1964-73 (2013).
Cho et al., "Therapeutic nanoparticles for drug delivery in cancer," Clin Cancer Res. 14(5):1310-6 (2008).
Choi et al., Mechanism for the endocytosis of spherical nucleic acid nanoparticle conjugates, Proc. Natl. Acad. Sci. U.S.A., 110: 7625 (2013).
Cook, Medicinal chemistry of antisense oligonucleotides—future opportunities, Anti-Cancer Drug Design, 6:585-607 (1991).
Cutler et al., Polyvalent nucleic acid nanostructures, J. Am. Chem. Soc., 133:9254 (2011).
Cutler et al., Polyvalent oligonucleotide iron oxide nanoparticle "click" conjugates, Nano Lett., 10:1477 (2010).
Cutler et al., Spherical nucleic acids, J. Am. Chem. Soc. 134: 1376 (2012).
Dave et al., Programmable assembly of DNA-functionalized liposomes by DNA, ACS Nano, 5:1304 (2011).
De Mesmaeker et al., Backbone modifications in oligonucleotides and peptide nucleic acid systems, Curr. Opin. in Struct. Biol., 5: 343-55 (1995).
Dua et al., "Liposome: Methods of Preparation and Applications," International Journal of Pharmaceutical Studies and Research, 3(2): 14-20 (7 pages) (2012).
Englisch et al., Angewandte Chemie, International Edition, 30:613-722 (1991).
Farokhzad et al., Nanomedicine: developing smarter therapeutic and diagnostic modalities, Drug Delivery Rev., 58:1456 (2006).
Ferrari, "Cancer nanotechnology: opportunities and challenges," Nature Reviews Cancer 5:161-71 (2005).
Freier et al., The ups and downs of nucleic acid duplex stability: structure-stability studies on chemically-modified DNA:RNA duplexes, Nucleic Acids Research, 25:4429-43 (1997).
Giljohann et al., Gene regulation with polyvalent siRNA-nanoparticle conjugates, J. Am. Chem. Soc., 131:2072 (2009).
Grijalvo et al., "Oligonucleotide delivery: a patent review (2010-2013)," Expert Opin Ther Pat. 24(7):801-19 (2014).
Gunnarsson et al., Liposome-Based Chemical barcodes for Single Molecule DNA Detection Using Imaging Mass Spectrometry, Nano. Lett., 10:732-37 (2010).
Gunnarsson et al., Single-Molecule Detection and Mismatch Discrimination of Unlabeled DNA Targets, Nano Lett., 8:183-8 (2008).
Hope et al., "Generation of Multilamellar and Unilamellar Phospholipid Vesicles," Chemistry and Physics of Lipids 40:89-107 (1986).
Hope et al., Production of large unilamellar vesicles by a rapid extrusion procedure: characterization of size distribution, trapped volume and ability to maintain a membrane potential, Biochim. Biophys. Acta., 812:55-65 (1985).

(56) References Cited

OTHER PUBLICATIONS

Houot et al., "T-cell modulation combined with intratumoral CpG cures lymphoma in a mouse model without the need for chemotherapy," Blood 113(15):546-3552 (2009).
Hurst et al., Maximizing DNA loading on a range of gold nanoparticle sizes, Anal. Chem., 78:8313 (2006).
International Preliminary Report on Patentability, United States Patent Office, PCT/US2014/068429, dated Jun. 7, 2016.
International Search Report and Written Opinion of the International Search Authority, United States Patent Office, PCT/US2014/068429, dated Aug. 10, 2015.
Jahn et al., "Microfluidic Directed Formation of Liposomes of Controlled Size," Langmuir 23(11): 6289-93 (5 pages) (2007).
Jakobsen et al., Assembly of liposomes controlled by triple helix formation, Bioconjugate Chem., 24:1485-95 (2013).
Jensen et al., Spherical nucleic acid nanoparticle conjugates as an RNAi-based therapy for glioblastoma, Sci. Trans. Med., 5:209ra152 (2013).
Kandimalla et al., "Secondary structures in CpG oligonucleotides affect immunostimulatory activity," Biochemical and Biophysical Research Communications 306:948-953 (2003).
Kasuya et al., "Bio-nanocapsule-liposome conjugates for in vivo pinpoint drug and gene delivery," Chapter 8, Methods Enzymol. 464:147-66 (2009).
Kelly et al., "Targeted Liposomal Drug Delivery to Monocytes and Macrophages," Journal of Drug Delivery, Article ID 727241, pp. 1-11 (2011).
Kim et al., "Cationic solid lipid nanoparticles reconstituted from low density lipoprotein components for delivery of siRNA," Mol Pharm. 5(4):622-31 (2008).
Kim et al., Effect of bovine serum albumin on the stability of methotrexate-encapsulated liposomes, Arch. Pharmacal Res., 14:336 (1991).
Kreig, "Toll-like receptor 9 (TLR9) agonists in the treatment of cancer," Oncogene 27:116-67 (2008).
Kroschwitz ed., The Concise Encyclopedia Of Polymer Science And Engineering, John Wiley & Sons, 858-9 (1990).
Laouini et al., "Preparation, Characterization and Applications of Liposomes: State of the Art," Journal of Colloid Science and Biotechnology 1:148-68 (2012).
Lee et al., "Imageable Antigen-Presenting Gold Nanoparticle Vaccines for Effective Cancer Immunotherapy In vivo", Angewandte Chemie International Edition, 51(35), 8800-8805 (2012).
Lee et al., Silver nanoparticle-oligonucleotide conjugates based on DNA with triple cyclic disulfide moieties, Nano Lett., 7: 2112 (2007).
Lesieur et al., "Size analysis and stability study of lipid vesicles by high-performance gel exclusion chromatography, turbidity. and dynamic light scattering," Analytical Biochemistry 192(2):334-43 (Abstract Only) (1991).
Li et al., "Combination Delivery of Antigens and CpG by Lanthanides-Based Core-Shell Nanoparticles for Enhanced Immune Response and Dual-Mode Imaging," Advanced Healthcare Materials 2(10):1309-1313 (2013).
Li et al., "Molecular spherical nucleic acids," PNAS pp. 1-5 (2018).
Li et al., "Nucleolin-targeting liposomes guided by aptamer AS1411 for the delivery of siRNA for the treatment of malignant melanomas," Biomaterials 35(12):3840-50 (2014).
Li et al., Reversible and Chemically Programmable Micelle Assembly with DNA Block-Copolymer Amphiphiles, Nano Lett., 4:1055 (2004).
Li et al., Thermal stability of DNA functionalized gold nanoparticles, Bioconjugate Chem., 24:1790-7 (2013).
Lin et al., "Gold Nanoparticle Delivery of Modified CpG Stimulates Macrophases and Inhibits Tumor Growth for Enhanced Immunotherapy", PLOS ONE, 8(5):e63550 9 pages (2013).
Liu et al., "Membrane anchored immunostimulatory oligonucleotides for in vivo cell modification and localized immunotherapy," Angew Chem Int Ed Engl. 50(31):7052-5 (2011).
Liu et al., "Silica Nanoparticle Supported Lipid Bilayers for Gene Delivery," Chem. Commun. 5100-5102 (2009).
Liu et al., DNA-based micelles: synthesis, micellar properties and size-dependent cell permeability, Chemistry, 16:3791-7 (2010).
Lytton-Jean et al., Highly Cooperative Behavior of Peptide Nucleic Acid Linked DNA Modified Gold Nanoparticle and Comb Polymer Aggregates, Advanced Materials, 21: 706 (2009).
Mangsbo et al., "Enhanced Tumor Eradication by Combining CTLA-4 or PD-1 Blockage with CpG Therapy", Journal of Immunotherapy 33(3):225-235 (2010).
Martin et al.,Ein neur Zugang zu 2'-O-alkylribonucleosiden and Eigenschaften deren oligonucleotide Hely. Chim. Acta, 78:486-504 (1995).
Massich et al., "Regulating Immune Response Using Polyvalent Nucleic Acid-Gold Nanoparticle Conjugates", Molecular Pharmaceutics 6(6):1934-1940 (2009).
McAllister et al., Polymeric nanogels produced via inverse microemulsion polymerization as potential gene and antisense delivery agents, J. Am. Chem. Soc. 124:15198 (2002).
Mirkin et al., A DNA-based method for rationally assembling nanoparticles into macroscopic materials, Natur, 382:607-9 (1996).
Mohamed et al., "Effect of toll-like receptor 7 and 9 targeted therapy to prevent the development of hepatocellular carcinoma," Liver Int. 35(3):1063-76 (2015).
Mohamed et al., "TLR9 mediates *S. aureus* killing inside osteoblasts via induction of oxidative stress," BMC Microbiology, 16: article 230, 8 pages (2016).
Nielsen et al., Sequence-selective recognition of DNA by strand displacement with a thymine-substituted polyamide, Science, 254:1497-500 (1991).
Nikolov et al., "Bias-dependent admittance in hybrid bilayer membranes," Langmuir. 22(17):7156-8 (2006).
Ozpolat et al., "Nanomedicine based approaches for the delivery of siRNA in cancer," J. Intern. Med. 267(1):44-53 (2010).
Patel et al., Scavenger receptors mediate cellular uptake of polyvalent oligonucleotide-functionalized gold nanoparticles, Bioconj. Chem., 21:2250 (2010).
Peter et al., "Characterization of suppressive oligodeoxynucleotides that inhibit Toll-like receptor-9-mediated activation of innate immunity," Immunology. 123(1):118-28 (2008).
Pfeiffer et al., Bivalent Cholesterol-Based Coupling of Oligonucleotides to Lipid Membrane Assemblies J. Am. Chem. Soc., 126, 10224-10225 (2004).
Pfeiffer et al., Quantification of oligonucleotide modifications of small unilamellar lipid vesicles, Anal. Chem., 78:7493-8 (2006).
Prigodich et al., Nano-flares for mRNA regulation and detection, ACS Nano, 3:2147 (2009).
Radovic-Moreno, et al., "Immunomodulatory spherical nucleic acids", PNAS 112(13):3892-3897 (2015).
Rosi et al., Nanostructures in biodiagnostics, Chem. Rev., 105:1547 (2005).
Rosi et al., Oligonucleotide-modified gold nanoparticles for intracellular gene regulation. Science 312: 1027 (2006).
Sanghvi, Chapter 15, Antisense Research and Application, Ed. S. T. Crooke and B. Lebleu, CRC Press, (1993).
Seferos et al., "Polyvalent DNA nanoparticle conjugates stabilize nucleic acids," Nano Lett. 9(1):308-11 (2009).
Seferos et al., Locked nucleic acid-nanoparticle conjugates, ChemBioChem, 8:1230 (2007).
Senior et al., Stability of small unilamellar liposomes in serum and clearance from the circulation: the effect of the phospholipid and cholesterol components, Life Sci. 30:2123 (1982).
Sokolova et al., "The use of calcium phosphate nanoparticles encapsulating Toll-like receptor ligands and the antigen hemagglutinin to induce dendritic cell maturation and T cell activation", Biomaterials 31:5627-5633 (2010).
Stengel et al., Determinants for Membrane Fusion Induced by Cholesterol-Modified DNA Zippers, J. Phys. Chem. B., 112:8264-74 (2008).
Stengel et al., DNA-Induced Programmable Fusion of Phospholipid Vesicles, J. Am. Chem. Soc., 129:9584-5 (2007).
Sulkowski et al., The influence of temperature, cholesterol content and pH on liposome stability, J. Mol. Struct., 744-747: 737 (2005).

(56) References Cited

OTHER PUBLICATIONS

Switaj et al., "CpG Immunostimulatory Oligodeoxynucleotide 1826 Enhances Antitumor Effect of Interleukin 12 Gene-Modified Tumor Vaccine in a Melanoma Model in Mice," Clinical Cancer Research 10:4165-4175 (2004).
Tincer et al., "Immunostimulatory activity of polyscchariderpoly (I:C) nanoparticles," Biomaterial 32(18):4275-4282 (2011).
Versluis et al., In situ modification of plain liposomes with lipidated coiled coil forming peptides induces membrane fusion, J. Am. Chem. Soc.. 135:8057 (2013).
Wei et al., "Polyvalent Immunostimulatory Nanoagents with Self-Assembled CpG Oligonucleotide-Conjugated Gold Nanoparticles", Angewandte Chemie International Edition 51(5):1202-1206 (2012).
West et al., "Recognition and signaling by toll-like receptors," Annu Rev Cell Dev Biol. 22:409-37 (2006).
Whitehead et al., Knocking down barriers: advances in siRNA delivery, Nat. Rev. Drug. Discov., 8:129 (2009).
Willis et al., "Liposome-Anchored Vascular Endothelial Growth Factor Aptamers," Bioconjugate Chem. 9 573-582 (1998).
Willis et al., Liposome-Anchored Vascular Endothelial Growth Factor Aptamers, Biocon. Chem., 9:573-82 (1998).
Wilson et al., "pH-Responsive Nanoparticle Vaccines for Dual-Delivery of Antigens and Immunostimulatory Oligonucleotides", ACS Nano, 7(5):3912-3925 (2013).
Wu et al., "DNA aptamer-micelle as an efficient detection/delivery vehicle toward cancer cells," Proc Natl Acad Sci U S A. 107(1):5-10 (2010).
Xing et al., Selective delivery of an anticancer drug with aptamer-functionalized liposomes to breast cancer cells in vitro and in vivo, J. Mater. Chem. B., 1:5288 (2013).
Yin et al., "Supramolecular self-assembled nanoparticles mediate oral delivery of therapeutic TNF-? siRNA against systemic inflammation," Angew Chem Int Ed Engl. (22):5757-61 (2013).
Young et al., Hollow spherical nucleic acids for intracellular gene regulation based upon biocompatible silica shells, Nano Lett., 12:3867 (2012).
Zhang et al., "Informational Liposomes: Complexes Derived from Cholesteryl-conjugated Oligonucleotides and Liposomes," Tetrahedron Letters 37(35):6243-6246 (1996).
Zhang et al., A general approach to DNA-programmable atom equivalents, Nat. Mater., 12:741 (2013).
Zhang et al., Antibody-linked spherical nucleic acids for cellular targeting, J. Am. Chem. Soc., 134:16488-91 (2012).
Zhang et al., PowerBLAST: a new network BLAST application for interactive or automated sequence analysis and annotation, *Genome Res.* 7:649:56 (1997).
Zhang et al., Structure-activity relationships of cationic shell-crosslinked knedel-like nanoparticles: shell composition and transfection efficiency/cytotoxicity, Biomaterials, 31:1805 (2010).
Zheng et al., "A spherical nucleic acid platform based on self-assembled DNA biopolymer for high-performance cancer therapy," ACS Nano. 7(8):6545-54 (2013).
Zheng et al., Aptamer nano-flares for molecular detection in living cells, Nano Lett., 9: 3258 (2009).
[No Author Listed] Modern Pharmaceutical Design. 2006. Chapter 5. p. 273. English language summary. 2 pages.
Aissaoui et al., Efficient topical delivery of plasmid DNA to lung in vivo mediated by putative triggered, PEGylated pDNA nanoparticles, *J .Control Release.* 154:275-84 (2011).
Ballas et al., Induction of NK activity in murine and human cells by CpG motifs in oligodeoxynucleotides and bacterial DNA. J Immunol. Sep. 1, 1996;157(5):1840-5.
Chan et al., Lipid-anchored DNA mediates vesicle fusion as observed by lipid and content mixing. Biointerphases. Jun. 2008;3(2):FA17. doi: 10.1116/1.2889062.
Chandaroy et al., Temperature-controlled content release from liposomes encapsulating Pluronic F127. J Control Release. Sep. 11, 2001;76(1-2):27-37. doi: 10.1016/s0168-3659(01)00429-1.
De Titta et al., Nanoparticle conjugation of CpG enhances adjuvancy for cellular immunity and memory recall at low dose. Proc Natl Acad Sci U S A. Dec. 3, 2013;110(49):19902-7. doi: 10.1073/pnas. 1313152110. Epub Nov. 18, 2013.
Ding et al., A statistical sampling algorithm for RNA secondary structure prediction. Nucleic Acids Res. Dec. 15, 2003;31(24):7280-301. doi: 10.1093/nar/gkg938.
Dunn et al., Reductively responsive siRNA-conjugated hydrogel nanoparticles for gene silencing. J Am Chem Soc. May 2, 2012;134(17):7423-30. Doi: 10.1021/ja300174v. Epub Apr. 19, 2012. Author Manuscript, 18 pages.
Fang et al., Cancer cell membrane-coated nanoparticles for anticancer vaccination and drug delivery. Nano Lett. 2014;14(4):2181-8. Doi: 10.1021/nl500618u. Epub Mar. 28, 2014.
Israelachvili et al., Physical principles of membrane organization. Q Rev Biophys. May 1980;13(2):121-200. doi: 10.1017/s0033583500001645.
Kaczmarek et al., 2,-Linking of lipids and other functions to uridine through 1,2,3-triazoles and membrane anchoring of the amphiphilic products. Eur J Org Chem. Mar. 1, 2010; 2010(8):1579-86. DOI: 10.1002/ejoc.200901073.
Karathanasis et al., Selective targeting of nanocarriers to neutrophils and monocytes. Ann Biomed Eng. Oct. 2009;37(10):1984-92. doi: 10.1007/s10439-009-9702-5. Epub Apr. 23, 2009.
Kim et al., pH-responsive biodegradable assemblies containing tunable phenyl-substituted vinyl ethers for use as efficient gene delivery vehicles. ACS Appl Mater Interfaces. Jun. 26, 2013;5(12):5648-58. Doi: 10.1021/am400977t. Epub Jun. 17, 2013. Author Manuscript, 28 pages.
Kusmierz et al., Defining the Design Parameters for in Vivo Enzyme Delivery Through Protein Spherical Nucleic Acids. ACS Cent Sci. May 27, 2020;6(5):815-822. doi: 10.1021/acscentsci.0c00313. Epub Apr. 27, 2020.
Li et al., Targeted delivery of antisense oligodeoxynucleotide and small interference RNA into lung cancer cells. Mol Pharm. Sep.-Oct. 2006;3(5):579-88. doi: 10.1021/mp060039w. Publication Date: Jul. 12, 2006.
Manoharan et al., Lipidic nucleic acids. Tetrahedron Letters. May 22, 1995;36(21):3651-4.
Periyasamy et al., Nanomaterials for the local and targeted delivery of osteoarthritis drugs. J Nanomater. 2012:2012:Article 673968. 13 pages. doi:0.1155/2012/673968.
Perrault et al., Mediating tumor targeting efficiency of nanoparticles through design. Nano Lett. May 2009;9(5):1909-15. Doi: 10.1021/nl900031y.
Raouane et al., Lipid conjugated oligonucleotides: a useful strategy for delivery. Bioconjug Chem. Jun. 20, 2012;23(6):1091-104. doi: 10.1021/bc200422w. Epub Mar. 15, 2012.
Rubenstein et al., Antisense oligonucleotide intralesional therapy for human PC-3 prostate tumors carried in athymic nude mice. J Surg Oncol. Jul. 1996;62(3):194-200. doi: 10.1002/(SICI)1096-9098(199607)62:3<194::AID-JSO9>3.0.CO;2-2.
Samadikhah et al., Preparation, characterization, and efficient transfection of cationic liposomes and nanomagnetic cationic liposomes. Int J Nanomedicine. 2011;6:2275-83. doi: 10.2147/IJN.S23074. Epub Oct. 12, 2011.
Townson et al., Re-examining the size/charge paradigm: differing in vivo characteristics of size- and charge-matched mesoporous silica nanoparticles. J Am Chem Soc. Oct. 30, 2013;135(43):16030-3. doi: 10.1021/ja4082414. Epub Oct. 16, 2013. Author Manuscript, 13 pages.
Tran et al., Targeting V600EB-Raf and Akt3 using nanoliposomal-small interfering RNA inhibits cutaneous melanocytic lesion development. Cancer Res. Sep. 15, 2008;68(18):7638-49. doi: 10.1158/0008-5472.CAN-07-6614.
Wang et al., Co-delivery of drugs and DNA from cationic core-shell nanoparticles self-assembled from a biodegradable copolymer. Nat Mater. Oct. 2006;5(10):791-6. doi: 10.1038/nmat1737. Epub Sep. 24, 2006. PMID: 16998471.
Wang et al., Nanometer-sized semiconductor clusters: materials synthesis, quantum size effects, and photophysical properties. J. Phys. Chem. Jan. 1, 1991;95(2):525-32. doi: 10.1021/j100155a009. Epub May 1, 2002.

(56) References Cited

OTHER PUBLICATIONS

Zammarchi et al., Antitumorigenic potential of STAT3 alternative splicing modulation. Proc Natl Acad Sci U S A. Oct. 25, 2011;108(43):17779-84. doi: 10.1073/pnas.1108482108. Epub Oct. 17, 2011.

* cited by examiner

A)

DNA loading = N(DNA) / N(liposomes)

$$N(total) = \frac{4\pi(d/2)^2 + 4\pi(d/2 - h)^2}{\alpha}$$

$$N(liposomes) = \frac{C(lipid) \cdot N_A \cdot V}{N(total)}$$

N(total) – number of lipids per liposome
$N_A$ – Avogadro number
d – particle diameter by DLS
h – thickness of the lipid bilayer (5 nm)
α – footprint of the lipid head group
(DOPC 0.71 nm²)

B)

SEQUENCE LISTING

```
<160> NUMBER OF SEQ ID NOS: 8

<210> SEQ ID NO 1
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 1
tttttttttt tttttttttt ttttt                                          25

<210> SEQ ID NO 2
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 2
aaaaaaaaaa tctcttgga                                                 19

<210> SEQ ID NO 3
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 3
tgcgtagaca aaaaaaaa                                                  19

<210> SEQ ID NO 4
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 4
```

```
acgcatctgt ccaagaga                                                  18

<210> SEQ ID NO 5
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 5
ctccatggtg ctcacttttt ttttt                                          25

<210> SEQ ID NO 6
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 6
ctccatggtg ctcacttttt ttttt                                          25

<210> SEQ ID NO 7
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 7
gagctgcacg ctgccgtcat ttttttttt                                      29

<210> SEQ ID NO 8
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 8
tcgtcgtttt gtcgttttgt cgtt                                           24
```

LIPOSOMAL PARTICLES, METHODS OF MAKING SAME AND USES THEREOF

This application is a Continuation of U.S. application Ser. No. 16/242,704, filed Jan. 8, 2019, which is a Continuation of U.S. application Ser. No. 15/101,523, filed Jun. 3, 2016, which is a U.S. National Phase of International Patent Application No. PCT/US14/68429, filed Dec. 3, 2014, which claims the priority benefit under 35 U.S.C. § 119(e) of U.S. Provisional Application No. 61/911,334, filed Dec. 3, 2013, and U.S. Provisional Application No. 61/982,269, filed Apr. 21, 2014, the disclosures of which are incorporated herein by reference in their entirety.

STATEMENT OF GOVERNMENT INTEREST

This invention was made with government support under HR0011-13-2-0018 awarded by the Defense Advanced Research Project Agency and CA151880 awarded by the National Institutes of Health. The government has certain rights in the invention.

SEQUENCE LISTING

This application contains, as a separate part of the disclosure, a Sequence Listing in computer readable form (filename: 2013-201_SeqListing.txt; Created: Dec. 3, 2014; 1,893 bytes), which is incorporated by reference in its entirety.

FIELD OF THE INVENTION

The present disclosure relates to liposomal particles, methods of making the same, and uses thereof. Liposomal particles are useful in gene regulation and drug delivery.

BACKGROUND

Chemistry has been explored to create liposomes and small unilamellar vesicles (SUVs). For example, Vogel et al., "DNA Controlled Assembly of Lipid Membranes," U.S. Patent Publication Number 2010/0144848, discloses that DNA modified with two lipophilic anchors can form liposomes or SUVs. This post modification technique does not favor high surface density modification.

Hook et al., "Oligonucleotides Related to Lipid Membrane Attachment," U.S. Patent Publication Number 2013/0252852 describes liposomes or SUVs created having an oligonucleotide having a first strand and a second strand of nucleic acid and two or more hydrophobic anchoring moieties located in its terminal ends, wherein the hydrophobic anchoring moieties are found in the bilayer. Since two cholesterol molecules are used to anchor a molecule into the lipid bilayer, this post modification technique does not favor high surface density modification.

Lu et al., "Amphiphilic Substances and Functionalized Lipid Vesicles Including the Same," U.S. Patent Publication Number 2010/0166842 describes liposomes or SUVs comprising at least two nucleotide segments hybridized with each other. This non-post modification technique based vesicle is less efficient in stabilizing vesicles since it incorporates stabilizing moieties on both sides of the lipid bilayer.

Non-patent literature also reveals chemistry to create liposomes and SUVs, but each of these chemistries has its issues too. For example, "Liposome-Anchored Vascular Endothelial Growth Factor Aptamers" *Bioconjugate Chem.*, 1998, 9, 573-582, describes the synthesis of aptamer DNA-functionalized liposomes and their application toward selective cancer cell targeting. The liposomes created by this method averaged 80 nanometers in size, had aptamer DNA molecules on both sides of the bilipid layer, and did not demonstrate gene regulation.

"Reversible Cell-Specific Drug Delivery with Aptamer-Functionalized Liposomes" *Angew. Chem. Int. Ed.* 2009, 48, 6494-6498, describes the synthesis of aptamer DNA-functionalized liposomes and their application toward selective cancer cell targeting and drug delivery. The liposomes created by this method averaged between 140 nanometers and 200 nanometers, utilize a cholesterol unit to anchor DNA into the lipid bilayer, comprise apatamer DNA molecules on both sides of the bilipid layer, and did not exhibit gene regulation.

"Selective delivery of an anticancer drug with aptamer-functionalized liposomes to breast cancer cells in vitro and in vivo" *J. Mater. Chem. B*, 2013, 1, 5288, discloses the synthesis of aptamer DNA-functionalized liposomes and their application toward selective cancer cell targeting and drug delivery. This work is an extension of the research disclosed in "Reversible Cell-Specific Drug Delivery with Aptamer-Functionalized Liposomes" above Like before, these particles utilize a cholesterol unit to anchor DNA into the lipid bilayer, comprise aptamer DNA molecules on both sides of the bilipid layer, and did not exhibit gene regulation.

The research in "Phospholipid Membranes Decorated by Cholesterol-Based Oligonucleotides as Soft Hybrid Nanostructures" *J. Phys. Chem. B*, 2008, 112, 10942-10952, characterizes cholesterol DNA-functionalized liposomes. In this report, liposomes of 33 to 35 nm in size were prepared from 1-Palmitoyl-2-oleoylphosphatidylcholine (POPC) lipid and post functionalized with cholesterol modified DNA molecule. This report does not demonstrate gene regulation, and these particles utilize a cholesterol unit to anchor DNA into the lipid bilayer.

"Bivalent Cholesterol-Based Coupling of Oligonucleotides to Lipid Membrane Assemblies" *J. Am. Chem. Soc.* 2004, 126, 10224-10225, describes the development of partially duplexed DNA strand containing two cholesterol units for anchoring into the lipid bilayer. The use of two cholesterol units to anchor a DNA strand into the lipid bilayer results in decreased surface density of oligonucleotides associated with the liposome.

In "Quantification of Oligonucleotide Modifications of Small Unilamellar Lipid Vesicles" *Anal. Chem.* 2006, 78, 7493-7498, the researchers describe the development of a technique for the quantification of DNA strands on a functionalized liposomal nanoparticle. The particle described comprises a partially duplexed DNA strand containing two cholesterol units for anchoring into the lipid bilayer. The use of two cholesterol units to anchor a DNA strand into the lipid bilayer results in decreased surface density of oligonucleotides associated with the liposome.

"Single-Molecule Detection and Mismatch Discrimination of Unlabeled DNA Targets" *Nano Lett.* 2008, 8, 183-188, discloses 100 nanometer sized liposomes functionalized with partially duplexed DNA strand containing two cholesterol units. This work is an extension of the research disclosed in "Bivalent Cholesterol-Based Coupling of Oligonucleotides to Lipid Membrane Assemblies" and "Quantification of Oligonucleotide Modifications of Small Unilamellar Lipid Vesicles" above. Like before, these particles comprise a partially duplexed DNA strand containing two cholesterol units for anchoring into the lipid bilayer. The use of the two cholesterol units to anchor a DNA strand into the lipid bilayer results in decreased surface density of oligonucleotides associated with the liposome.

"DNA-Induced Programmable Fusion of Phospholipid Vesicles" *J. Am. Chem. Soc.* 2007, 129, 9584-9585, is an analytical paper on the fusion of cholesterol DNA-functionalized liposomal nanoparticles. The vesicles utilized in this paper were at least 100 nanometers in size.

"Determinants for Membrane Fusion Induced by Cholesterol-Modified DNA Zippers" *J. Phys. Chem. B,* 2008, 112, 8264-8274, is an analytical paper on fusion of cholesterol DNA-functionalized liposomal nanoparticle, and is a continuation of the work from "DNA-Induced Programmable Fusion of Phospholipid Vesicles" described above. This paper combines sequence specific fusion with the utilization of a partially duplexed DNA strand containing two cholesterol units to anchor the oligonucleotide into the lipid bilayer (e.g., the partially duplexed DNA strand found in "Quantification of Oligonucleotide Modifications of Small Unilamellar Lipid Vesicles" above).

"Liposome-Based Chemical barcodes for Single Molecule DNA Detection Using Imaging Mass Spectrometry" *Nano Lett.,* 2010, 10, 732-737, is an analytical paper on detection of specific DNA targets depending on the DNA sequence. This is an extension of the work from the same group that reported "DNA-Induced Programmable Fusion of Phospholipid Vesicles" that combines sequence specific fusion with different DNA anchoring (using bischolesteryl anchor, see: *Anal. Chem.* 2006, 78, 7493-7498).

"Programmable Assembly of DNA-Functionalized Liposomes by DNA" is an analytical paper that discloses the assembly of cholesterol DNA functionalized liposomes. In this report, liposomes with a hydrodynamic diameter of 114 and 251 nm were synthesized and post synthetically functionalized with cholesterol modified DNA molecules. The particles in this report utilize cholesterol anchoring of the oligonucleotide molecule into the lipid bilayer.

SUMMARY OF THE INVENTION

Liposomes are spherical, self-closed structures in a varying size range consisting of one or several hydrophobic lipid bilayers with a hydrophilic core. The diameter of these lipid based carriers range from 0.15-1 micrometers, which is significantly higher than an effective therapeutic range of 20-100 nanometers. Liposomes termed small unilamellar vesicles (SUV), can be synthesized in the 20-50 nanometer size range, but encounter challenges such as instability and aggregation leading to inter-particle fusion. This inter-particle fusion limits the use of SUVs in therapeutics.

To combat this instability, SUVs can be functionalized with polymers, peptides, DNA, and other molecules of interest by two distinct techniques. In a first approach, a modified molecule of interest is added to the mixture of lipids, lipid film or hydration buffer during the synthesis of liposome. This approach results in a liposomes containing a functional molecule of interest on both inner and outer layers of the liposomal membrane. Generally speaking, structures created by this method are not stable at a size smaller than 80 nanometers (nm). In an alternative approach, a SUV may be made by anchoring a substrate of interest into the lipid bilayer of the preformed vesicle (a "post modification technique"). This alternative approach yields a liposomal nanoparticle containing a functional molecule of interest on the outer layer of the liposomal membrane. Importantly, this alternative post modification approach allows the creation of liposome of any size, even less than 50 nanometers.

Accordingly, in one aspect the disclosure provides an architecture comprising a lipophilic end and a non-lipophilic end. The lipophilic end, in some embodiments, comprises tocopherol. In additional embodiments, the tocopherol is chosen from the group consisting of alpha-tocopherol, beta-tocopherol, gamma-tocopherol and delta-tocopherol.

The non-lipophilic end, in further embodiments, is a charged polymer. In some embodiments, the charged polymer is an oligonucleotide. In related embodiments, the oligonucleotide comprises RNA or DNA, and in various embodiments the RNA is an inhibitory RNA (RNAi) that performs a regulatory function. In still further embodiments, the RNAi is selected from the group consisting of a small inhibitory RNA (siRNA), an RNA that forms a triplex with double stranded DNA, and a ribozyme. In additional embodiments, the RNA is a piwi-interacting RNA (piRNA), or the RNA is a microRNA that performs a regulatory function. In some embodiments, the DNA is antisense-DNA.

In another aspect, the disclosure provides a method for making an architecture of the disclosure, the method comprising providing an oligonucleotide, providing a phosphoramidite-modified-tocopherol, and exposing said oligonucleotide to said phosphoramidite-modified-tocopherol to make an architecture of the disclosure.

In a further aspect, a liposomal particle is provided by the disclosure, said liposomal particle having a substantially spherical geometry, said liposomal particle comprising a lipid bilayer comprising a plurality of lipid groups; and an oligonucleotide.

It is contemplated by the disclosure, in various embodiments, that said plurality of lipid groups comprises a lipid selected from the group consisting of the phosphatidylcholine, phosphatidylglycerol, and phosphatidylethanolamine family of lipids.

In various embodiments, said lipid is selected from the group consisting of 1,2-dioleoyl-sn-glycero-3-phosphocholine (DOPC), 1,2-dimyristoyl-sn-phosphatidylcholine (DMPC), 1-palmitoyl-2-oleoyl-sn-phosphatidylcholine (POPC), 1,2-distearoyl-sn-glycero-3-phospho-(1'-rac-glycerol) (DSPG), 1,2-dioleoyl-sn-glycero-3-phospho-(1'-rac-glycerol) (DOPG), 1,2-distearoyl-sn-glycero-3-phosphocholine (DSPC), 1,2-dipalmitoyl-sn-glycero-3-phosphocholine (DPPC), 1,2-di-(9Z-octadecenoyl)-sn-glycero-3-phosphoethanolamine (DOPE), and 1,2-dihexadecanoyl-sn-glycero-3-phosphoethanolamine (DPPE).

In further embodiments, the oligonucleotide is an oligonucleotide-lipid conjugate containing a lipophilic tethered group, wherein said lipophilic tethered group is adsorbed into the lipid bilayer. The lipophilic tethered group comprises, in various embodiments, tocopherol or cholesterol.

The disclosure also contemplates that the tocopherol, in various embodiments, is selected from the group consisting of a tocopherol derivative, alpha-tocopherol, beta-tocopherol, gamma-tocopherol and delta-tocopherol. In yet further embodiments, the disclosure also contemplates that the lipophilic tethered group (i.e., the lipid anchor) comprises, for example and without limitation, palmitoyl, dipalmitoyl, stearyl, or distearyl.

The oligonucleotide, in further embodiments, comprises RNA or DNA. In additional embodiments, the RNA is a non-coding RNA, and in still further embodiments, the non-coding RNA is an inhibitory RNA (RNAi). The disclosure further contemplates that, in some embodiments, the RNAi is selected from the group consisting of a small inhibitory RNA (siRNA), a single-stranded RNA (ssRNA) that forms a triplex with double stranded DNA, and a ribozyme. In further embodiments, the RNA is a microRNA. In some embodiments, the DNA is antisense-DNA.

In various embodiments, the diameter of said liposomal particle is less than or equal to about 50 nanometers. Regarding the surface density, the disclosure provides compositions and methods wherein a liposomal particle comprises from about 10 to about 100 oligonucleotides, or from about 10 to about 80 oligonucleotides. In some embodiments, the particle comprises 70 oligonucleotides.

In some embodiments, the oligonucleotide is a modified oligonucleotide.

In another aspect of the disclosure, a method of making a liposomal particle is provided, the method comprising adding a phospholipid to a solvent to form a first mixture, said first mixture comprising a plurality of liposomes; disrupting said plurality of liposomes to create a second mixture, said second mixture comprising a liposome and a small unilamellar vesicle (SUV); isolating said SUV from said second mixture, said SUV having a particle size between about 20 nanometers and 50 nanometers; and adding an oligonucleotide to the isolated SUV to make the liposomal particle.

In some embodiments, the particle size of the plurality of liposomes in said first mixture is between about 100 nanometers and 150 nanometers. In further embodiments, the particle size of the liposome and the SUV in said second mixture is between about 20 nanometers and about 150 nanometers. In still further embodiments, the liposomal particle has a particle size less than or equal to about 50 nanometers.

In some embodiments, the oligonucleotide is an oligonucleotide-lipid conjugate containing a lipophilic tethered group, wherein said lipophilic tethered group is adsorbed into the lipid bilayer. In related embodiments, the lipophilic tethered group comprises tocopherol or cholesterol. In further embodiments, tocopherol is chosen from the group consisting of a tocopherol derivative, alpha-tocopherol, beta-tocopherol, gamma-tocopherol and delta-tocopherol.

In further embodiments, the oligonucleotide comprises RNA or DNA. The RNA, in some embodiments, is a non-coding RNA. In further embodiments, the non-coding RNA is an inhibitory RNA (RNAi). The disclosure further contemplates that, in additional embodiments, the RNAi is selected from the group consisting of a small inhibitory RNA (siRNA), a single-stranded RNA (ssRNA) that forms a triplex with double stranded DNA, and a ribozyme.

In some embodiments, the RNA is a microRNA. In various embodiments, the DNA is antisense-DNA.

In some embodiments, the oligonucleotide is a modified oligonucleotide.

In another aspect of the disclosure, a method of inhibiting expression of a gene is provided comprising the step of hybridizing a polynucleotide encoding said gene product with one or more oligonucleotides complementary to all or a portion of said polynucleotide, said oligonucleotide being attached to the liposomal particle of the disclosure, wherein hybridizing between said polynucleotide and said oligonucleotide occurs over a length of said polynucleotide with a degree of complementarity sufficient to inhibit expression of said gene product.

In some embodiments, expression of said gene product is inhibited in vivo. In further embodiments, expression of said gene product is inhibited in vitro.

In additional embodiments, the liposomal particle has a diameter about less than or equal to 50 nanometers. In some embodiments, the oligonucleotide comprises RNA or DNA. The RNA, in some embodiments, is a non-coding RNA. In related embodiments, the non-coding RNA is an inhibitory RNA (RNAi). The disclosure also contemplates that the RNAi, in various embodiments, is selected from the group consisting of a small inhibitory RNA (siRNA), a single-stranded RNA (ssRNA) that forms a triplex with double stranded DNA, and a ribozyme. In some embodiments, the RNA is a microRNA. In further embodiments, the DNA is antisense-DNA.

In another aspect of the disclosure, a method for up-regulating activity of a toll-like receptor (TLR) is provided, comprising contacting a cell having the toll-like receptor with a liposomal particle of the disclosure. In some embodiments, the oligonucleotide is a TLR agonist. In further embodiments, the toll-like receptor is chosen from the group consisting of toll-like receptor 1, toll-like receptor 2, toll-like receptor 3, toll-like receptor 4, toll-like receptor 5, toll-like receptor 6, toll-like receptor 7, toll-like receptor 8, toll-like receptor 9, toll-like receptor 10, toll-like receptor 11, toll-like receptor 12, and toll-like receptor 13.

In a further aspect, the disclosure provides a method for down-regulating activity of a toll-like receptor (TLR), comprising contacting a cell having the toll-like receptor with a liposomal particle of the disclosure. In some embodiments, the oligonucleotide is a TLR antagonist. In further embodiments, the toll-like receptor is chosen from the group consisting of toll-like receptor 1, toll-like receptor 2, toll-like receptor 3, toll-like receptor 4, toll-like receptor 5, toll-like receptor 6, toll-like receptor 7, toll-like receptor 8, toll-like receptor 9, toll-like receptor 10, toll-like receptor 11, toll-like receptor 12, and toll-like receptor 13.

The disclosure also contemplates that, in various embodiments, a method as disclosed herein is performed in vitro. In further embodiments, the disclosure contemplates that a method as disclosed herein is performed in vivo.

DETAILED DESCRIPTION

Figure 1:
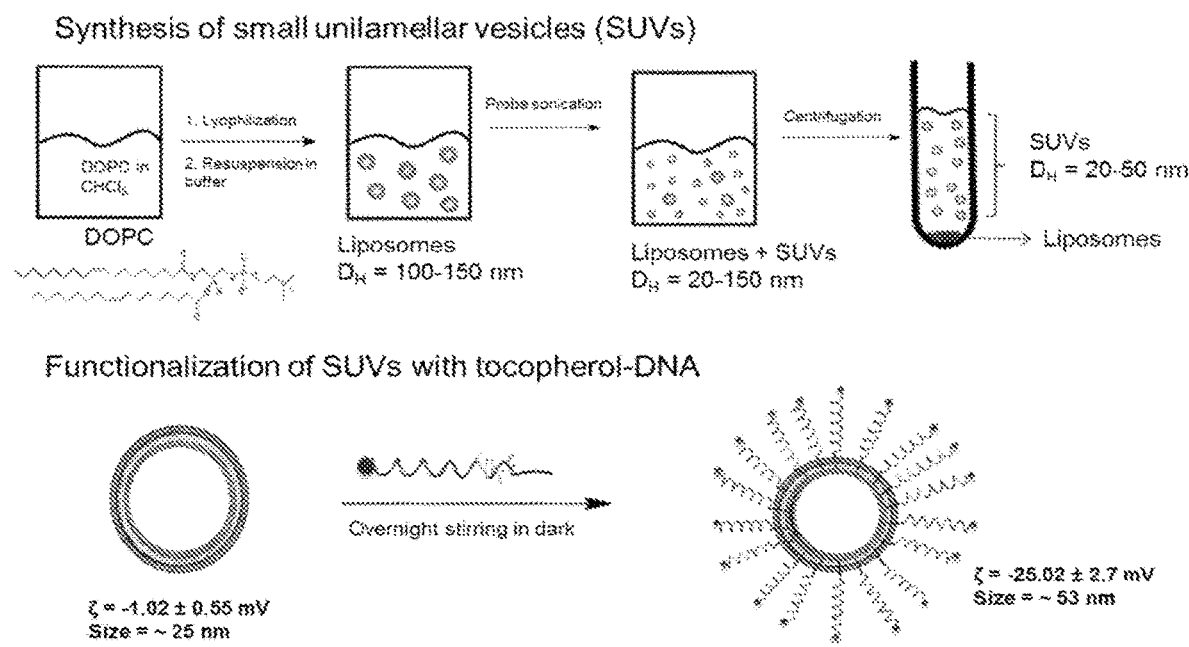
FIG. 1 depicts the synthesis of small unilamellar vesicles (SUV) functionalized with DNA or RNA on the surface of lipid vesicle. The larger size liposomes are sonicated into SUVs using a probe sonicator, and are separated from heavy impurities by ultracentrifugation.

Spherical nucleic acid (SNA) nanoparticle conjugates are structures typically synthesized from inorganic nanoparticle templates and shells of highly oriented nucleic acid ligands immobilized on the surface of such particles [Mirkin et al., Nature 382: 607 (1996)]. SNAs have been prepared in a variety of different forms [Cutler et al., J. Am. Chem. Soc. 134: 1376 (2012); Will et al., In Nanomaterials for Biomedicine; American Chemical Society: Vol. 1119, p 1-20 (2012)]. Core compositions, including gold, silica [Young et al., Nano Lett. 12: 3867 (2012)], iron oxide [Cutler et al., Nano Lett. 10: 1477 (2010); Zhang et al., Nat. Mater. 12: 741 (2013)], and Ag [Lee et al., Nano Lett. 7: 2112 (2007)] with shell compositions consisting of DNA, RNA, LNA [Seferos et al., ChemBioChem 8: 1230 (2007)], and PNA [Lytton-Jean et al., Advanced Materials 21: 706 (2009)] have all been prepared and explored. Hollow SNA structures consisting of cross-linked oligonucleotide [Cutler et al., J. Am. Chem. Soc. 133: 9254 (2011)] have been synthesized along with micelle-block copolymer structures [Li et al., Nano Lett. 4: 1055 (2004); Alemdaroglu et al., Advanced Materials 20: 899 (2008); Liu et al., Chemistry—A European Journal 16: 3791 (2010); Chien et al., Chem. Commun. 47: 167 (2011)]. Although there is now a tremendous structural and compositional diversity among the known SNAs, they all share some common properties and features. Their polyvalent architectures allow them to cooperatively bind oligonucleotides and form duplex structures that exhibit very narrow melting transitions. These properties have been exploited in the development of high sensitivity and high selectivity genomic detection systems [Rosi et al., Chem. Rev. 105: 1547 (2005)]. While linear nucleic acids do not enter cells well without polymer, peptide, or viral transfection agents, the three-dimensional SNA structure is recognized by class A scavenger receptors [Patel et al., Bioconjugate Chem. 21: 2250 (2010); Choi et al., Proc. Natl. Acad. Sci. U.S.A. 110: 7625 (2013)] and is rapidly taken into over 60 different cell types without the need for an ancillary transfection agent [McAllister et al., J. Am. Chem. Soc. 124: 15198 (2002); Whitehead et al., Nat Rev Drug Discov 8: 129 (2009); Zhang et al., Biomaterials 31: 1805 (2010)]. This property has made such structures important elements in strategies for both intracellular detection [Zheng et al., Nano Lett. 9: 3258 (2009); Prigodich et al., ACS Nano 3: 2147 (2009)] and gene regulation via antisense or siRNA pathways [Rosi et al., Science 312: 1027 (2006); Agbasi-Porter et al., Bioconjugate Chem. 17: 1178 (2006); Giljohann et al., J. Am. Chem. Soc. 131: 2072 (2009); Jensen et al., Science Translational Medicine 5: 209ra152 (2013)].

The barrier to therapeutic use is high, however, especially when such structures are made from materials that have known problems with clearance or unknown biodistribution characteristics. Ideally, one would like an SNA structure that is made from readily available starting materials, can be synthesized at scale, and consists of components that have been a part of FDA approved pharmaceuticals [Cutler et al., J. Am. Chem. Soc. 134: 1376 (2012); Farokhzad et al., Drug Delivery Rev. 58: 1456 (2006)]. Herein, a strategy for making such structures is provided, which consist of small liposomal cores stabilized with a dense shell of a charged polymer with a hydrophobic tail that can intercalate between the phospholipids that define the liposome structure. One such charged polymer contemplated for use is a nucleic acid. As with conventional SNAs, these liposomal structures rapidly enter multiple cell lines and are used in some embodiments to effectively knockdown gene expression via antisense pathways. Conventional SNAs have been shown to enter cells derived from many organs and tissues, including Breast (SKBR3, MDA-MB-231, AU-565), Brain (U87, LN229, U118), Bladder (HT-1376, 5637, T24), Colon (LS513), Cervix (HeLa, SiHa), Skin (C166, KB, MCF 10A), Kidney (MDCK), Brain (Rat Hippocampus Neurons, Astrocytes, Glial Cells), Bladder, Blood (PBMC, T-cells), Pancreas (Human β-Islets), Skin (Human), Blood (Sup T1, Jurkat), Leukemia (K562), Liver (HepG2), Kidney (293T), Ovary (CHO), Fibroblast (NIH3T3), Macrophage (RAW264.7). The spherical nucleic acid architecture facilitates the entry of these constructs into cells by binding to scavenger receptor A, a cell-membrane receptor. A few non-limiting examples of cell lines which express this receptor are HeLa, SKOV-3, U87, Neuro 2A, RAW cells, HepG2, Hep3B, MDA-MB-468, MCF-7, C8S, C166 Bend3, A549, Rab9, HeyA8, Jurkat cells.

The major drawback of employment of SUVs is their inherent instability in solution due to high propensity to fuse into bigger liposomal structures. It is disclosed herein that functionalization of these structures with a dense layer of negatively charged DNA increases their stability by, e.g., decreasing particle-particle interaction due to the repulsion of the negatively charged particle surfaces. In the course of the studies described herein, it was found that tocopherol functionalized DNA provides higher density of DNA strands on the particle compared to other known hydrophobic DNA analogues, significantly increasing stability of the particle. In addition to the general colloidal stability, high density of the DNA will increase the uptake of this nanoparticle via a scavenger receptor B pathway and will allow efficient delivery of the genetic material into a cell. Finally, the dense layer of DNA is expected to increase particle stability in a body, its circulation rate, and therefore improve bio distribution of this nanomedicine.

The present disclosure teaches that by increasing the surface negative charge of SUVs, via the attachment of anionic entities including, but not limited to, DNA and RNA, the colloidal stability of these vesicles is increased. Additionally, the dense spherical arrangement and radial orientation of nucleic acids exhibits unique chemical and biological properties, unlike their linear counterparts. These spherical nucleic acids (SNA) are non-toxic and though anionic, can efficiently enter cells without the aid of ancillary cationic transfection agents in a non-immunogenic fashion. These exceptional properties allow their use as delivery agents for gene regulation in different therapies. The liposome-template mediated synthesis of SNAs provides an alternative platform to metal core SNAs which limits SNAs therapeutic diversity with bioaccumulation of the metal core and inability to encapsulate therapeutic entities.

Tocopherol modified oligonucleotides and methods of making such oligonucleotides, liposomal particles and methods of making same, and uses of liposomal particles now will be described more fully hereinafter. Indeed, the disclosure may be embodied in many different forms and should not be construed as limited to the embodiments set forth herein. These embodiments are provided in sufficient written detail to describe and enable one skilled in the art to make and use the invention, along with disclosure of the best mode for practicing the invention, as defined by the claims and equivalents thereof.

Likewise, many modifications and other embodiments of the methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Terminology

Unless defined otherwise, all technical and scientific terms used herein have the same meaning as commonly understood by one of skill in the art to which the invention pertains. Although any methods and materials similar to or equivalent to those described herein can be used in the practice or testing of the invention, the preferred methods and materials are described herein.

Certain terms are first defined. Additional terms are defined throughout the specification.

For the sake of brevity, a description of an embodiment of the disclosure in terms of a small unilamellar vesicle (SUV), a liposomal SNA (LSNA), a liposomal particle, or a spherical nucleic acid (SNA) may also be applicable to an embodiment that uses any of the other foregoing terms. By way of example, a method of regulating gene expression using a liposomal SNA may also be described herein as a method of regulating gene expression using a liposomal particle. Small unilamellar vesicles (SUVs) are liposomal particles of sub-100 nanometer size and are used as the precursors to LSNAs. SUVs and LSNAs, as such, can be considered subclasses of liposomal particles.

Terms used herein are intended as "open" terms (for example, the term "including" should be interpreted as "including but not limited to," the term "having" should be interpreted as "having at least," the term "includes" should be interpreted as "includes but is not limited to").

Furthermore, in those instances where a convention analogous to "at least one of A, B and C, etc." is used, in general such a construction is intended in the sense of one having ordinary skill in the art would understand the convention (for example, "a system having at least one of A, B and C" would include but not be limited to systems that have A alone, B alone, C alone, A and B together, A and C together, B and C together, and/or A, B, and C together). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A or B" or "A and B."

All language such as "from," "to," "up to," "at least," "greater than," "less than," and the like include the number recited and refer to ranges which can subsequently be broken down into sub-ranges as discussed above.

A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use an aspect of a described embodiment or feature contained in the same, or a definitive decision to use a specific skill regarding a described embodiment or feature contained in the same. In this latter context, the modal verb "may" has the same meaning and connotation as the auxiliary verb "can."

As used herein, the articles "a" and "an" refer to one or to more than one (for example, to at least one) of the grammatical object of the article.

"About" and "approximately" shall generally mean an acceptable degree of error for the quantity measured given the nature or precision of the measurements. Exemplary degrees of error are within 20-25 percent (%), typically, within 10%, and more typically, within 5% of a given value or range of values.

The chemical structures described herein are named according to IUPAC nomenclature rules and include art-accepted common names and abbreviations where appropriate. The IUPAC nomenclature can be derived with chemical structure drawing software programs, such as ChemDraw® (PerkinElmer, Inc.), ChemDoodle® (iChemLabs, LLC) and Marvin (ChemAxon Ltd.). The chemical structure controls in the disclosure to the extent that an IUPAC name is misnamed or otherwise conflicts with the chemical structure disclosed herein.

Headings, for example, (A), (B), (i) etc., are presented merely for ease of reading the specification and claims. The use of headings in the specification or claims does not require the steps or elements be performed in alphabetical or numerical order or the order in which they are presented.

The present disclosure describes novel particles, termed liposomal particles, methods of making the same, and uses of these particles. The present liposomal particles are advantageous over other known liposomal based materials in that they are stable at a particle size that is smaller than other known liposomal particles, and the dense layer of DNA increases particle stability in a body, and therefore increases the circulation rate of liposomal vesicles, which improves bio-distribution of these particles inside the body.

A. Tocopherol Modified Oligonucleotides

In a first embodiment, an architecture comprising a tocopherol modified oligonucleotide is disclosed. A tocopherol-modified oligonucleotide comprises a lipophilic end and a non-lipophilic end. The lipophilic end comprises tocopherol, and may be chosen from the group consisting of a tocopherol derivative, alpha-tocopherol, beta-tocopherol, gamma-tocopherol and delta-tocopherol. The lipophilic end, in further embodiments, comprises palmitoyl, dipalmitoyl, stearyl, or distearyl.

The non-lipophilic end of the tocopherol-modified oligonucleotide is an oligonucleotide. The oligonucleotide is either RNA or DNA. The RNA can be an inhibitory RNA (RNAi) that performs a regulatory function, and is chosen from the group consisting of a small RNAi that is selected from the group consisting of a small inhibitory RNA (siRNA), an RNA that forms a triplex with double stranded DNA, and a ribozyme. Alternatively, the RNA is microRNA that performs a regulatory function. In still further embodiments, the RNA is a piwi-interacting RNA (piRNA). The DNA is, in some embodiments, an antisense-DNA.

Oligonucleotides contemplated for use according to the disclosure are from about 5 to about 100 nucleotides in length. Methods and compositions are also contemplated wherein the oligonucleotide is about 5 to about 90 nucleotides in length, about 5 to about 80 nucleotides in length, about 5 to about 70 nucleotides in length, about 5 to about 60 nucleotides in length, about 5 to about 50 nucleotides in length about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, about 5 to about 10 nucleotides in length, and all oligonucleotides intermediate in length of the sizes specifically disclosed to the extent that the oligonucleotide is able to achieve the desired result. Accordingly, oligonucleotides of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100 nucleotides in length are contemplated.

Modified Oligonucleotides

Specific examples of oligonucleotides include those containing modified backbones or non-natural internucleoside linkages. Oligonucleotides having modified backbones include those that retain a phosphorus atom in the backbone and those that do not have a phosphorus atom in the backbone. Modified oligonucleotides that do not have a phosphorus atom in their internucleoside backbone are considered to be within the meaning of "oligonucleotide."

Modified oligonucleotide backbones containing a phosphorus atom include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Also contemplated are oligonucleotides having inverted polarity comprising a single 3' to 3' linkage at the 3'-most internucleotide linkage, i.e. a single inverted nucleoside residue which may be abasic (the nucleotide is missing or has a hydroxyl group in place thereof). Salts, mixed salts and free acid forms are also contemplated. Representative United States patents that teach the preparation of the above phosphorus-containing linkages include, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, the disclosures of which are incorporated by reference herein.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages; siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. See, for example, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, the disclosures of which are incorporated herein by reference in their entireties.

In still other embodiments, oligonucleotide mimetics wherein both one or more sugar and/or one or more internucleotide linkage of the nucleotide units are replaced with "non-naturally occurring" groups. In one aspect, this embodiment contemplates a peptide nucleic acid (PNA). In PNA compounds, the sugar-backbone of an oligonucleotide is replaced with an amide containing backbone. See, for example U.S. Pat. Nos. 5,539,082; 5,714,331; and 5,719,262, and Nielsen et al., 1991, *Science*, 254: 1497-1500, the disclosures of which are herein incorporated by reference.

In still other embodiments, oligonucleotides are provided with phosphorothioate backbones and oligonucleosides with heteroatom backbones, and including —$CH_2$—NH—O—$CH_2$—, —$CH_2$—N($CH_3$)—O—$CH_2$—, —$CH_2$—O—N($CH_3$)—$CH_2$—, —$CH_2$—N($CH_3$)—N($CH_3$)—$CH_2$— and —O—N($CH_3$)—$CH_2$—$CH_2$— described in U.S. Pat. Nos. 5,489,677, and 5,602,240. Also contemplated are oligonucleotides with morpholino backbone structures described in U.S. Pat. No. 5,034,506.

In various forms, the linkage between two successive monomers in the oligonucleotide consists of 2 to 4, desirably 3, groups/atoms selected from —$CH_2$—, —O—, —S—, —$NR^H$—, >C=O, >C=$NR^H$, >C=S, —Si(R")$_2$—, —SO—, —S(O)$_2$—, —P(O)$_2$—, —PO($BH_3$)—, —P(O,S)—, —P(S)$_2$—, —PO(R")—, —PO($OCH_3$)—, and —PO($NHR^H$)—, where RH is selected from hydrogen and $C_{1-4}$-alkyl, and R" is selected from $C_{1-6}$-alkyl and phenyl. Illustrative examples of such linkages are —$CH_2$—$CH_2$—$CH_2$—, —$CH_2$—CO—$CH_2$—, —$CH_2$—CHOH—$CH_2$—, —O—$CH_2$—O—, —O—$CH_2$—$CH_2$—, —O—$CH_2$—CH= (including $R^5$ when used as a linkage to a succeeding monomer), —$CH_2$—$CH_2$—O—, —$NR^H CH_2$—$CH_2$—, —$CH_2CH_2$—$NR^H$—, —$CH_2$—$NR^H$—$CH_2$—, —O—$CH_2$—$CH_2$—$NR^H$—, —$NR^H$—CO—O—, —$NR^H$—CO—$NR^H$—, —$NR^H$—CS—$NR^H$—, —$NR^H$—C(=$NR^H$)—$NR^H$—, —$NR^H$—CO—$CH_2$—$NR^H$—O—CO—O—, —O—CO—$CH_2$—O—, —O—$CH_2$—CO—O—, —$CH_2$—CO—$NR^H$—, —O—CO—$NR^H$—, —$NR^H$—CO—$CH_2$—, —O—$CH_2$—CO—$NR^H$—, —O—$CH_2$—$CH_2$—$NR^H$—, —CH=N—O—, —$CH_2$—$NR^H$—O—, —$CH_2$—O—N= (including $R^5$ when used as a linkage to a succeeding monomer), —$CH_2$—O—$NR^H$—, —CO—$NR^H$—$CH_2$—, —$CH_2$—$NR^H$—O—, —$CH_2$—$NR^H$—CO—, —O—$NR^H$—$CH_2$—, —O—$NR^H$—, —O—$CH_2$—S—, —S—$CH_2$—O—, —$CH_2$—$CH_2$—S—, —O—$CH_2$—$CH_2$—S—, —S—$CH_2$—CH= (including $R^5$ when used as a linkage to a succeeding monomer), —S—$CH_2$—$CH_2$—, —S—$CH_2$—$CH_2$—O—, —S—$CH_2$—$CH_2$—S—, —$CH_2$—S—$CH_2$—, —$CH_2$—SO—$CH_2$—, —$CH_2$—$SO_2$—$CH_2$—, —O—SO—O—, —O—$S(O)_2$—, —O—$S(O)_2$—O—, —O—$S(O)_2$—$CH_2$—, —O—$S(O)_2$—$NR^H$—, —$NR^H$—$S(O)_2$—$CH_2$—; —O—$S(O)_2$—$CH_2$—, —O—$P(O)_2$—O—, —O—P(O,S)—O—, —O—$P(S)_2$—O—, —S—$P(O)_2$—O—, —S—P(O,S)—O—, —S—$P(S)_2$—O—, —O—$P(O)_2$—S—, —O—P(O,S)—S—, —O—$P(S)_2$—S—, —S—$P(O)_2$—S—, —S—P(O,S)—S—, —S—$P(S)_2$—S—, —O—PO(R")—O—, —O—PO($OCH_3$)—O—, —O—PO($OCH_2CH_3$)—O—, —O—PO(O $CH_2CH_2$S—R)—O—, —O—PO($BH_3$)—O—, —O—PO($NHR^N$)—O—, —O—$P(O)_2$—$NR^H$ H—, —$NR^H$—$P(O)_2$—O—, —O—P(O,$NR^H$)—O—, —$CH_2$—$P(O)_2$—O—, —O—P(O)$_2$ —$CH_2$—, and —O—Si(R")$_2$—O—; among which —$CH_2$—CO—$NR^H$—, —$CH_2$—$NR^H$—O—, —S—$CH_2$—O—, —O—$P(O)_2$—O—O—P(—O,S)—O—, —O—$P(S)_2$—O—, —$NR^H$ $P(O)_2$—O—, —O—P(O,$NR^H$)—O—, —O—PO(R")—O—, —O—PO($CH_3$)—O—, and —O—PO($NHR^N$)—O—, where RH is selected form hydrogen and $C_{1-4}$-alkyl, and R" is selected from $C_{1-6}$-alkyl and phenyl, are contemplated. Further illustrative examples are given in Mesmaeker et. al., 1995, *Current Opinion in Structural Biology*, 5: 343-355 and Susan M. Freier and Karl-Heinz Altmann, 1997, *Nucleic Acids Research*, vol 25: pp 4429-4443.

Still other modified forms of oligonucleotides are described in detail in U.S. Patent Application No. 20040219565, the disclosure of which is incorporated by reference herein in its entirety.

Modified oligonucleotides may also contain one or more substituted sugar moieties. In certain aspects, oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Other embodiments include O[($CH_2$)$_n$O]$_m CH_3$, O($CH_2$)$_n OCH_3$, O($CH_2$)$_n NH_2$, O($CH_2$)$_n CH_3$, O($CH_2$)$_n ONH_2$, and O($CH_2$)$_n ON[($CH_2$)$_n CH_3$]$_2$, where n and m are from 1 to about 10. Other oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. In one aspect, a modification includes 2'-methoxyethoxy (2'-O—$CH_2CH_2OCH_3$, also known as 2'-O-(2-methoxyethyl) or 2'-MOE) (Martin et al., 1995, *Helv. Chim. Acta*, 78: 486-504) i.e., an alkoxyalkoxy group. Other modifications include 2'-dimethylaminooxyethoxy, i.e., a O($CH_2$)$_{20}$N($CH_3$)$_2$ group, also known as 2'-DMAOE, as described in examples herein below, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—N($CH_3$)$_2$, also described in examples herein below.

Still other modifications include 2'-methoxy (2'-O—$CH_3$), 2'-aminopropoxy (2'-O$CH_2CH_2CH_2NH_2$), 2'-allyl (2'-$CH_2$—CH=$CH_2$), 2'-O-allyl(2'-O—$CH_2$—CH=$CH_2$) and 2'-fluoro (2'-F). The 2'-modification may be in the arabino (up) position or ribo (down) position. In one aspect, a 2'-arabino modification is 2'-F. Similar modifications may also be made at other positions on the oligonucleotide, for example, at the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. See, for example, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, the disclosures of which are incorporated herein by reference in their entireties.

In one aspect, a modification of the sugar includes Locked Nucleic Acids (LNAs) in which the 2'-hydroxyl group is linked to the 3' or 4' carbon atom of the sugar ring, thereby forming a bicyclic sugar moiety. The linkage is in certain aspects is a methylene ($—CH_2—$)$_n$ group bridging the 2' oxygen atom and the 4' carbon atom wherein n is 1 or 2. LNAs and preparation thereof are described in WO 98/39352 and WO 99/14226.

Oligonucleotides may also include base modifications or substitutions. As used herein, "unmodified" or "natural" bases include the purine bases adenine (A) and guanine (G), and the pyrimidine bases thymine (T), cytosine (C) and uracil (U). Modified bases include other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine(1H-pyrimido[5, 4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzox-azin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified bases may also include those in which the purine or pyrimidine base is replaced with other heterocycles, for example 7-deaza-adenine, 7-deazaguanosine, 2-aminopyridine and 2-pyridone. Further bases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., 1991, *Angewandte Chemie, International Edition,* 30: 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing the binding affinity and include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects combined with 2'-O-methoxyethyl sugar modifications. See, U.S. Pat. Nos. 3,687,808, 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,750,692 and 5,681,941, the disclosures of which are incorporated herein by reference.

A "modified base" or other similar term refers to a composition which can pair with a natural base (e.g., adenine, guanine, cytosine, uracil, and/or thymine) and/or can pair with a non-naturally occurring base. In certain aspects, the modified base provides a $T_m$ differential of 15, 12, 10, 8, 6, 4, or 2° C. or less. Exemplary modified bases are described in EP 1 072 679 and WO 97/12896.

By "nucleobase" is meant the naturally occurring nucleobases adenine (A), guanine (G), cytosine (C), thymine (T) and uracil (U) as well as non-naturally occurring nucleobases such as xanthine, diaminopurine, 8-oxo-$N^6$-methyladenine, 7-deazaxanthine, 7-deazaguanine, $N^4,N^4$-ethanocytosin, N',N'-ethano-2,6-diaminopurine, 5-methylcytosine (mC), 5-($C^3$—$C^6$)-alkynyl-cytosine, 5-fluorouracil, 5-bromouracil, pseudoisocytosine, 2-hydroxy-5-methyl-4-tr-iazolopyridin, isocytosine, isoguanine, inosine and the "non-naturally occurring" nucleobases described in Benner et al., U.S. Pat. No. 5,432,272 and Susan M. Freier and Karl-Heinz Altmann, 1997, *Nucleic Acids Research,* vol. 25: pp 4429-4443. The term "nucleobase" thus includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., 1991, *Angewandte Chemie, International Edition,* 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). The term "nucleosidic base" or "base unit" is further intended to include compounds such as heterocyclic compounds that can serve like nucleobases including certain "universal bases" that are not nucleosidic bases in the most classical sense but serve as nucleosidic bases. Especially mentioned as universal bases are 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

B. Methods of Making Tocopherol Modified Oligonucleotides

In a second embodiment, methods of making tocopherol oligonucleotides are disclosed. First, an oligonucleotide and phosphoramidite-modified-tocopherol are provided. Then, the oligonucleotide is exposed to the phosphoramidite-modified-tocopherol to create the tocopherol modified oligonucleotide. While not meant to be limiting, any chemistry to one of skill in the art can be used to attach the tocopherol to the oligonucleotide, including amide linking or click chemistry.

C. Liposomal Particles

In a third embodiment, liposomal particles are disclosed. The liposomal particle has at least a substantially spherical geometry, an internal side and an external side, and comprises a lipid bilayer. The lipid bilayer is comprised of a first-lipid and a second-lipid. The first-lipid and second-lipid are, in some embodiments, the same. In further embodiments, the first-lipid and second-lipid are different.

The first-lipid is chosen from the phosphocholine family of lipids or the phosphoethanolamine family of lipids. While not meant to be limiting, the first-lipid is chosen from group consisting of 1,2-dioleoyl-sn-glycero-3-phosphocholine (DOPC), 1,2-dimyristoyl-sn-phosphatidylcholine (DMPC), 1-palmitoyl-2-oleoyl-sn-phosphatidylcholine (POPC), 1,2-distearoyl-sn-glycero-3-phospho-(1'-rac-glycerol) (DSPG), 1,2-dioleoyl-sn-glycero-3-phospho-(1'-rac-glycerol) (DOPG), 1,2-distearoyl-sn-glycero-3-phosphocholine (DSPC), 1,2-dipalmitoyl-sn-glycero-3-phosphocholine (DPPC), 1,2-di-(9Z-octadecenoyl)-sn-glycero-3-phosphoethanolamine (DOPE), and 1,2-dihexadecanoyl-sn-glycero-3-phosphoethanolamine (DPPE).

The second-lipid is chosen from the phosphocholine family of lipids or the phosphoethanolamine family of lipids. While not meant to be limiting, the second-lipid is chosen from group consisting of 1,2-dioleoyl-sn-glycero-3-phosphocholine (DOPC), 1,2-dimyristoyl-sn-phosphatidylcholine (DMPC), 1-palmitoyl-2-oleoyl-sn-phosphatidylcholine (POPC), 1,2-distearoyl-sn-glycero-3-phospho-(1'-rac-glycerol) (DSPG), 1,2-dioleoyl-sn-glycero-3-phospho-(1'-rac-glycerol) (DOPG), 1,2-distearoyl-sn-glycero-3-phosphocholine (DSPC), 1,2-dipalmitoyl-sn-glycero-3-phosphocholine (DPPC), 1,2-di-(9Z-octadecenoyl)-sn-glycero-3-phosphoethanolamine (DOPE), and 1,2-dihexadecanoyl-sn-glycero-3-phosphoethanolamine (DPPE).

The liposomal particle further comprises a tocopherol modified oligonucleotide wherein the lipophilic end of the tocopherol modified oligonucleotide is absorbed into the lipid bilayer. The tocopherol is chosen from the group consisting of alpha-tocopherol, beta-tocopherol, gamma-tocopherol and delta-tocopherol. The non-lipophilic end of the tocopherol modified oligonucleotide is an oligonucleotide. This oligonucleotide is, in various embodiments, either RNA or DNA. The RNA can be an inhibitory RNA (RNAi) that performs a regulatory function, and in various embodiments is selected from the group consisting of a small inhibitory RNA (siRNA), an RNA that forms a triplex with double stranded DNA, and a ribozyme. Alternatively, and in further embodiments, the RNA is microRNA that performs a regulatory function. The DNA is optionally an antisense-DNA. In still further embodiments, the RNA is a piwi-interacting RNA (piRNA).

Put another way, the disclosure provides a liposomal particle, said liposomal particle having a substantially spherical geometry, said liposomal particle comprising a lipid bilayer comprising a plurality of lipid groups; and an oligonucleotide. In various embodiments, the oligonucleotide is a modified oligonucleotide. In some embodiments, the plurality of lipid groups comprises a lipid selected from the group consisting of the phosphatidylcholine, phosphatidylglycerol, and phosphatidylethanolamine family of lipids. The oligonucleotide, in further embodiments is an oligonucleotide-lipid conjugate containing a lipophilic tethered group, wherein said lipophilic tethered group is adsorbed into the lipid bilayer. The lipophilic tethered group comprises, in various embodiments, tocopherol, palmitoyl, dipalmitoyl, stearyl, distearyl, or cholesterol.

Alternatively, the liposomal particle further comprises a therapeutic agent encapsulated on the internal side of the liposomal particle. In further embodiments, a liposomal particle of the disclosure further comprises a therapeutic agent that is either directly or indirectly attached to the liposomal particle. Indirect attachment includes, for example and without limitation, attachment to an oligonucleotide that is in turn attached to the liposomal particle.

In some embodiments, the liposomal particle further comprises a diagnostic agent encapsulated on the internal side of the liposomal particle. This diagnostic agent is in some embodiments gadolinium.

With respect to the surface density of oligonucleotides on the surface of a liposomal particle of the disclosure, it is contemplated that a liposomal particle as described herein comprises from about 1 to about 100 oligonucleotides on its surface. In various embodiments, a liposomal particle comprises from about 10 to about 100, or from 10 to about 90, or from about 10 to about 80, or from about 10 to about 70, or from about 10 to about 60, or from about 10 to about 50, or from about 10 to about 40, or from about 10 to about 30, or from about 10 to about 20 oligonucleotides on its surface. In further embodiments, a liposomal particle comprises at least about 5, 10, 20, 30, 40, 50, 60, 70, 80, 90, or 100 oligonucleotides on its surface.

D. Methods of Making Liposomal Particles

In a fourth embodiment, methods of making liposomal particles are disclosed. First, a phospholipid, solvent, and a tocopherol modified oligonucleotide are provided. Then, the phospholipid is added to the solvent to form a first mixture comprising liposomes. The size of the liposomes in the first mixture is between about 100 nanometers and about 150 nanometers.

Next, the liposomes are disrupted to create a second mixture comprising liposomes and small unilamellar vesicles (SUV). The size of the liposomes and SUVs in the second mixture is between about 20 nanometers and about 150 nanometers.

Next, the SUVs having a particle size between about 20 nanometers and about 50 nanometers are isolated from the second mixture. Finally, the tocopherol modified oligonucleotide is added to the isolated SUVs to make a liposomal particle.

The particle size of the liposomal particles created by a method of the disclosure is less than or equal to about 50 nanometers. In some embodiments, a plurality of liposomal particles is produced and the particles in the plurality have a mean diameter of less than or equal to about 50 nanometers (e.g., about 5 nanometers to about 50 nanometers, or about 5 nanometers to about 40 nanometers, or about 5 nanometers to about 30 nanometers, or about 5 nanometers to about 20 nanometers, or about 10 nanometers to about 50 nanometers, or about 10 nanometers to about 40 nanometers, or about 10 nanometers to about 30 nanometers, or about 10 nanometers to about 20 nanometers). In further embodiments, the particles in the plurality of liposomal particles created by a method of the disclosure have a mean diameter of less than or equal to about 20 nanometers, or less than or equal to about 25 nanometers, or less than or equal to about 30 nanometers, or less than or equal to about 35 nanometers, or less than or equal to about 40 nanometers, or less than or equal to about 45 nanometers.

Put another way, in some aspects the disclosure provides a method of making a liposomal particle, comprising adding a phospholipid to a solvent to form a first mixture, said first mixture comprising a plurality of liposomes; disrupting said plurality of liposomes to create a second mixture, said second mixture comprising a liposome and a small unilamellar vesicle (SUV); isolating said SUV from said second mixture, said SUV having a particle size between about 20 nanometers and 50 nanometers; and adding an oligonucleotide to the isolated SUV to make the liposomal particle.

E. Uses of Liposomal Particles in Gene Regulation/Therapy

Methods for inhibiting gene product expression provided herein include those wherein expression of the target gene product is inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or 100% compared to gene product expression in the absence of a liposome SNA. In other words, methods provided embrace those which results in essentially any degree of inhibition of expression of a target gene product.

The degree of inhibition is determined in vivo from a body fluid sample or from a biopsy sample or by imaging techniques well known in the art. Alternatively, the degree of inhibition is determined in a cell culture assay, generally as a predictable measure of a degree of inhibition that can be expected in vivo resulting from use of a specific type of liposomal SNA and a specific oligonucleotide.

In some aspects of the disclosure, it is contemplated that a liposomal particle performs both a gene inhibitory function as well as a therapeutic agent delivery function. In such aspects, a therapeutic agent is encapsulated in a liposomal particle of the disclosure and the particle is additionally functionalized with one or more oligonucleotides designed to effect inhibition of target gene expression. In further embodiments, a therapeutic agent is attached to a liposomal particle of the disclosure.

In various aspects, the methods include use of an oligonucleotide which is 100% complementary to the target polynucleotide, i.e., a perfect match, while in other aspects, the oligonucleotide is at least (meaning greater than or equal to) about 95% complementary to the polynucleotide over the length of the oligonucleotide, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20% complementary to the polynucleotide over the length of the oligonucleotide to the extent that the oligonucleotide is able to achieve the desired degree of inhibition of a target gene product.

It is understood in the art that the sequence of an antisense compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). The percent complementarity is determined over the length of the oligonucleotide. For example, given an antisense compound in which 18 of 20 nucleotides of the antisense compound are complementary to a 20 nucleotide region in a target polynucleotide of 100 nucleotides total length, the oligonucleotide would be 90 percent complementary. In this example, the remaining noncomplementary nucleotides may be clustered or interspersed with complementary nucleobases and need not be contiguous to each other or to complementary nucleotides. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

Accordingly, in a fifth embodiment, methods of utilizing liposomal particles in gene regulation therapy are provided. This method comprises the step of hybridizing a polynucleotide encoding said gene product with one or more oligonucleotides complementary to all or a portion of said polynucleotide, said oligonucleotide being attached to a liposomal particle, wherein hybridizing between said polynucleotide and said oligonucleotide occurs over a length of said polynucleotide with a degree of complementarity sufficient to inhibit expression of said gene product. The liposomal particle has a diameter that is about less than or equal to 50 nanometers. The inhibition of gene expression may occur in vivo or in vitro.

The oligonucleotide utilized in this method is either RNA or DNA. The RNA can be an inhibitory RNA (RNAi) that performs a regulatory function, and in various embodiments is selected from the group consisting of a small inhibitory RNA (siRNA), an RNA that forms a triplex with double stranded DNA, and a ribozyme. Alternatively, the RNA is microRNA that performs a regulatory function. The DNA is, in some embodiments, an antisense-DNA.

In another aspect of the disclosure, a liposomal particle is used in a method for treating a traumatic brain injury (TBI). In the United States, there have been over 244,000 cases of TBI in the military since 2000, and it is the leading cause of death and disability in people under the age of 45. Further, it is currently difficult to predict the neurological outcome of "mild severity" incidents, and the secondary phase of the injury (e.g., inflammation, ischemia, and apoptosis) is very difficult to treat.

Thus, in some embodiments, methods of the disclosure are directed to the use of a liposomal particle designed to target and regulate the expression of a gene product implicated in TBI. For example and without limitation, the target gene product is selected from the group consisting of histone deacetylase (HDAC), BCL2-associated X (BAX), a matrix metallopeptidase/metalloproteinase (MMP; including, without limitation, matrix metallopeptidase 9 (MMP-9)), a hypoxia-inducible factor (HIF; including, without limitation, hypoxia inducible factor 1 alpha (HIF1-α)), and calpain.

F. Use of Liposomal Particles in Immune Regulation

Toll-like receptors (TLRs) are a class of proteins, expressed in sentinel cells, that plays a key role in regulation of innate immune system. The mammalian immune system uses two general strategies to combat infectious diseases. Pathogen exposure rapidly triggers an innate immune response that is characterized by the production of immunostimulatory cytokines, chemokines and polyreactive IgM antibodies. The innate immune system is activated by exposure to Pathogen Associated Molecular Patterns (PAMPs) that are expressed by a diverse group of infectious microorganisms. The recognition of PAMPs is mediated by members of the Toll-like family of receptors. TLR receptors, such as TLR 4, TLR 8 and TLR 9 that response to specific oligonucleotide are located inside special intracellular compartments, called endosomes. The mechanism of modulation of TLR 4, TLR 8 and TLR9 receptors is based on DNA-protein interactions.

Synthetic immunostimulatory oligonucleotides that contain CpG motifs that are similar to those found in bacterial DNA stimulate a similar response of the TLR receptors. Therefore immunomodulatory ODNs have various potential therapeutic uses, including treatment of immune deficiency and cancer. Employment of liposomal nanoparticles functionalized with immunomodulatory ODNs will allow for increased preferential uptake and therefore increased therapeutic efficacy. Notably, smaller particles (25 to 40 nm) such as those provided herein penetrate tissue barriers more efficiently, therefore providing more effective activation of innate immune responses. Thus, small liposomal nanoparticles of 30 nm in size, functionalized with stabilized with functional CpG motif-containing DNA, would provide enhanced therapeutic effect.

Down regulation of the immune system would involve knocking down the gene responsible for the expression of the Toll-like receptor. This antisense approach involves use of liposomal nanoparticles functionalized with specific antisense oligonucleotide sequences to knock out the expression of any toll-like protein.

Accordingly, in a sixth embodiment, methods of utilizing liposomal particles for modulating toll-like receptors are disclosed. The method either up-regulates or down-regulates the Toll-like-receptor through the use of a TLR agonist or a TLR antagonist, respectively. The method comprises contacting a cell having a toll-like receptor with a liposomal particle. The toll-like receptors modulated include toll-like receptor 1, toll-like receptor 2, toll-like receptor 3, toll-like receptor 4, toll-like receptor 5, toll-like receptor 6, toll-like receptor 7, toll-like receptor 8, toll-like receptor 9, toll-like receptor 10, toll-like receptor 11, toll-like receptor 12, and toll-like receptor 13.

G. Use of Liposomal Particles in Nanoflare Technology

In additional aspects of the disclosure, a liposomal particle is used to detect an intracellular target. Such methods are disclosed in U.S. Pat. No. 8,507,200, which is incorporated by reference herein in its entirety.

Briefly, an oligonucleotide containing a recognition sequence that is specific for a target molecule is attached to a liposomal particle as described herein. Thus, "recognition sequence" as used herein is understood to mean a sequence that is partially or completely complementary to a target molecule of interest.

The liposomal particle with attached oligonucleotide containing a recognition sequence is initially associated with a reporter sequence. As used herein, a "reporter sequence" is understood to mean a sequence that is partially or completely complementary and therefore able to hybridize to the recognition sequence. The reporter sequence is labeled with a detectable label (such as, without limitation, a fluorophore), and is also referred to as a nanoflare. The reporter sequence is in various aspects comprised of fewer, the same or more bases than the recognition sequence, such that binding of the recognition sequence to its target molecule causes release of the hybridized reporter sequence, thereby resulting in a detectable and measurable change in the label attached to the reporter sequence.

The invention is illustrated by the following examples, which are not intended to be limiting in any way.

EXAMPLES

Example 1—General

All reagents were obtained from the suppliers in highest purity and used without any further purification. HPLC was performed on a Varian Prostar system. UV/Vis was recorded on a Varian Cary 300 spectrophotometer. Fluorescence spectra were obtained on a SPEX FluoroLog fluorometer.

Example 2—Synthesis of Oligonucleotides

Oligonucleotides were synthesized in 1.0 micromolar scale on an automated DNA synthesizer (ABI 3400, Applied Biosystems, Inc.). After cleavage and deprotection with aqueous ammonium hydroxide (55° C., 14 h), the DNA was purified by reverse-phase HPLC and quantified by UV spectrometer.

Example 3—Synthesis of Liposomal Particles

The lipid monomer (40 μmol of 1,2-dioleoyl-sn-glycero-3-phosphocholine (DOPC) dissolved in chloroform) was added to a 20 mL vial and then evaporated before overnight lyophilization to remove the solvent resulting in a thin lipid film. The film was then rehydrated with HBS buffer (5.0 mL, 20 mM Hepes buffer, 150 mM NaCl at pH 7.4) followed by vigorous mixing to form a liposomal suspension and was then probe-sonicated in an ice bath for 30 min without pulsating. The resulting suspension was then ultracentrifuged at 104,986 g and 4° C. for 90 min. The phospholipid concentration was calculated using elemental analysis.

Next, the DNA/RNA strands were synthesized with the α-tocopherol modification via standard solid-phase phosphoramidite chemistry on an Expedite Nucleotide Synthesis System. The strands were cleaved from the solid support and purified by reverse-phase high performance liquid chromatography.

Figure 13:
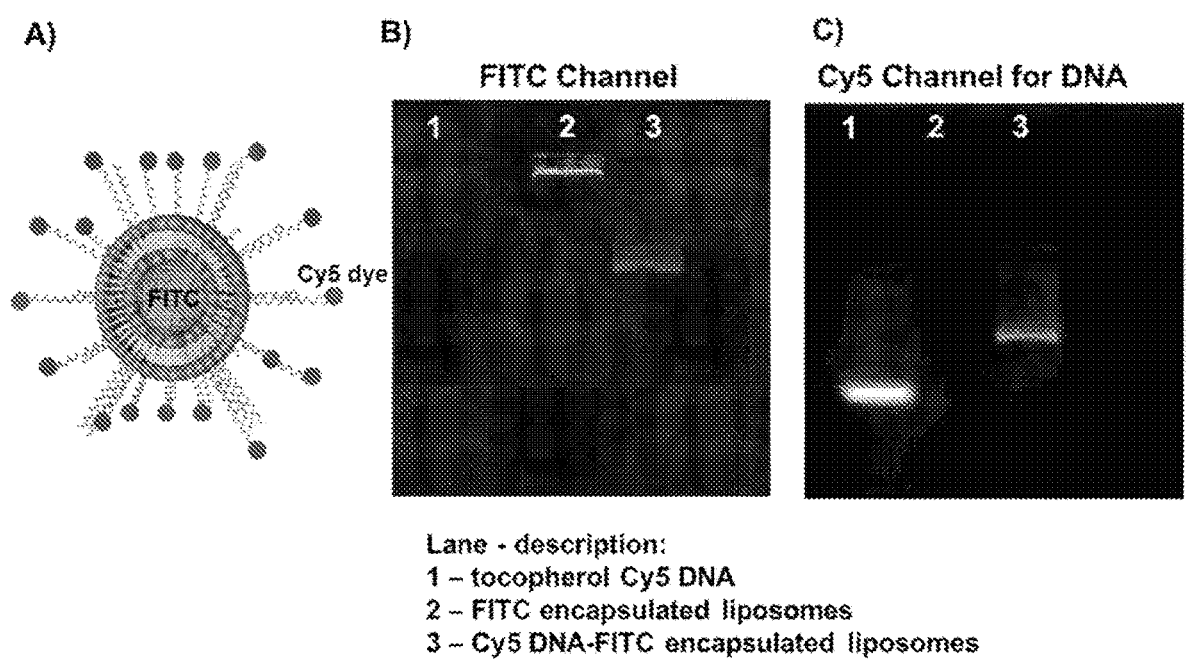
FIG. 13 shows the movement of FITC-encapsulated LSNAs that have been functionalized with 5'-Cy5-labeled DNA strand on a 1% agarose gel electrophoresis image. B) FITC channel showing movement of the liposomal core on the gel due to the presence of negatively charged DNA corona. C) Cy5 channel indicates the difference in mobility due to size differences between a free strand and those functionalized on the liposomal construct. Both channels co-localize on the same band.

Lastly, the appropriate DNA/RNA (16 μM) was added to the 1.3 mM solution of SUVs and allowed to stir overnight. The particles were then purified the next day by centrifugation filters with cut-off of 100 kDa. The particles were then analyzed via TEM and dynamic light scattering. Gel electrophoresis of liposomal particles encapsulated with FITC and surface functionalized with CY5-labeled DNA is shown in FIG. 13.

Example 4—Visualization of the Cellular Uptake of Liposomal Particles

Figure 5:
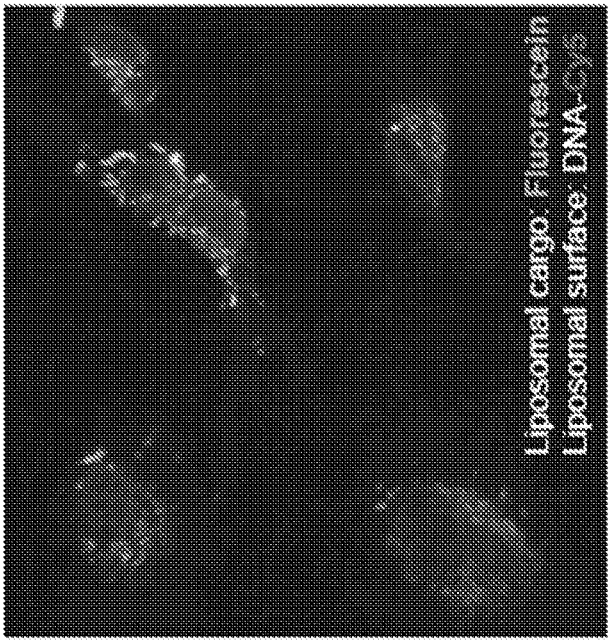
FIG. 5 comprises confocal images demonstrating that liposomal particles disclosed herein are able to enter cells. HeLa cells were treated with DNA ($dT_{30}$-Cy5 or $dT_{30}$) at a concentration of 100 nM in serum-free media and analyzed after 16 hours.
Figure 5:
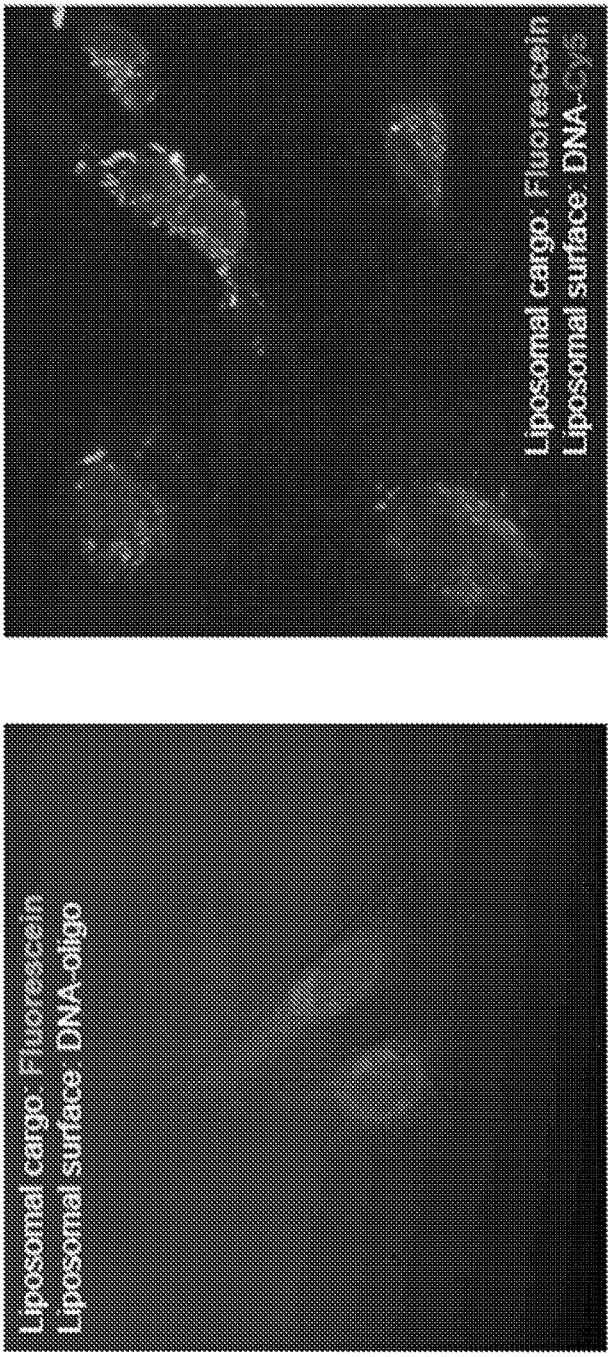
Figure 6:
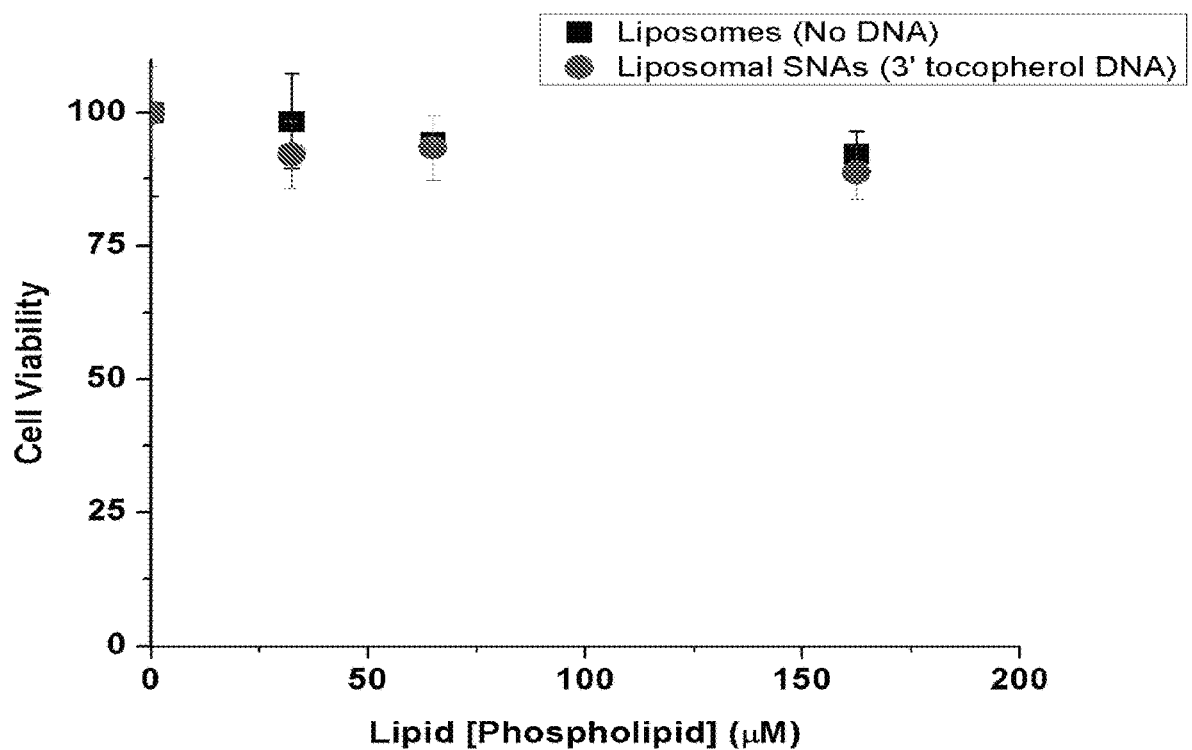
FIG. 6 shows cell viability assay data demonstrating that liposomes stabilized with tocopherol modified oligonucleotides do not exhibit a substantial cytotoxic effect on cells in comparison to liposomes left unmodified.

To visualize the cellular uptake of LSNAs, HeLa cells were grown on a Lab-Tek® II Chamber #1.5 German Coverglass System (Nalge Nunc International) overnight and incubated with Cy5-labled LSNAs (0.1 μM of DNA concentration). After 16 hours of incubation, the media was replaced with fresh media, and live cells were stained with Hoechst 33342 (Invitrogen) following the manufacturer's instructions. All images were obtained with a Zeiss 510 LSM at 40× magnification using a Mai Tai 3308 laser (Spectra-Physics). Fluorescence emission was collected at 390-465 nm and 650-710 nm, with excitation at 729 and 633 nm respectively (FIG. 5). The left panel of FIG. 5 shows entry of liposomal fluorescein into HeLa cells, while the right panel of FIG. 5 shows co-localization of fluorescein and Cy5 suggesting delivery of the entire liposome into the cell.

Example 4—Cell Viability

The cytotoxicity of liposomal particles was evaluated with a Alamar Blue® Assay (Invitrogen). Briefly, HeLa cells were seeded on a 96 well plate in 200 μL of media and incubated for 24 hours. The cells were then treated with FITC encapsulated bare SUVs and DNA functionalized LSNAs at varying concentrations of phospholipid concentrations (0, 32.5, 65, 162.5 μM). After 16 hours, medium was removed, cells were washed with PBS 3 times and then incubated with 90 μL fresh culture medium in addition to 10 μL of alamar blue reagent for 4 hours. They were then analyzed by checking the excitation at 560 nm and emission at 590 nm.

Example 5—Preparation of SUVs

Materials

The 1,2-dioleoyl-sn-glycero-3-phosphocholine lipid monomer (DOPC), were purchased from Avanti Polar Lipids, Inc. either in dry powder form or in a chloroform solution and used without further purification. Phosphoramidites and other DNA synthesis reagents were purchased from Glen Research, Inc., at the highest purity and were used as received from the manufacturer.

Instrumentation

Lyophilization was carried out using a Freezone Lyohilizer (Labconco, Kansas City, MO). Sonication was conducted using a titanium-alloy solid probe sonicator (500 watt Vibra-Cell™ VC 505, Sonics & Materials, Inc., Newtown, CT) set at 40% intensity of 20 kHz without pulsing. Ultracentrifugation was carried out using Beckman-Coulter Avanti J-30I (Beckmann-Coulter, Inc., Indianapolis, IN). Transmission electron microscopy (TEM) was performed using Hitachi-2300 STEM electron microscope. Dynamic light scattering (DLS) was collected using a Malvern Zetasizer Nano-ZS (Malvern Instruments, UK). MALDI-ToF analysis was performed using Bruker Autoflex III SmartBean mass spectrometer (Bruker Daltonics Inc., MA, USA). Fluorescence measurements were carried out on Fluorlog-3 system (HORIBA Jobin Yvon Inc., NJ, USA). UV-Vis spectroscopy was collected using Cary 5000 UV-Vis spectrophotometer. (Varian Inc., CA, USA).

Oligonucleotide Synthesis

The oligonucleotides were synthesized using automated solid-support phosphoramidite synthesis on an Expedite 8909 Nucleotide Synthesis System (MM48 Synthesizer, Bioautomation) using DCI as an activator. Tocopherol phosphoramidite was coupled via an automated protocol using extended 15 minutes coupling time. After the completion of solid phase synthesis, the oligonucleotide strands were cleaved from the solid support using an overnight treatment with aqueous ammonium hydroxide (28-30% aqueous solution, Aldrich), after which time the excess of the ammonia was removed using a gentle flow of nitrogen gas (house nitrogen was used). The oligonucleotides were purified using Microsorb C18 column on a reverse-phase high pressure liquid chromatography (HPLC, Varian) using a gradient of TEAA (triethylammonium acetate) buffer and acetonitrile (gradient: 10% v/v to 100% v/v acetonitrile over 30 min). The collected fractions containing product were concentrated on a lyophilizer. The obtained oligonucleotides were re-suspended in nanopure water and purity was analyzed using MALDI-TOF and denaturing acrylamide gel electrophoresis techniques.

TABLE 1

Oligonucleotide sequences used in the experiments.

| Name of the strand | Application | Sequence (5'-3') |
| --- | --- | --- |
| Cy5 labeled $T_{25}$ strand | Size analysis, DNA density determination and stability studies | 5'-Cy5-$T_{25}$-tocopherol-3' (SEQ ID NO: 1) |
| Melt strand 1 | Melt analysis | 5'-tocopherol-$A_{10}$-TCT CTT GGA-3' (SEQ ID NO: 2) |
| Melt strand 2 | Melt analysis | 5'-TGC GTA GAC-$A_{10}$ tocopherol-3' (SEQ ID NO: 3) |
| Linker strand | Melt analysis | 5'-ACG CAT CTG TCC AAG AGA-3' (SEQ ID NO: 4) |
| HER2 antisense | Gene regulation | 5'-CTC CAT GGT GCT CAC-$T_{10}$-tocopherol-3' (SEQ ID NO: 5) |
| Cy5 labeled HER2 antisense | Imaging and Cellular uptake | 5'-Cy5-CTC CAT GGT GCT CAC-$T_{10}$-tocopherol-3' (SEQ ID NO: 6) |
| Scrambled antisense | Gene regulation | 5'-GAG CTG CAC GCT GCC GTC A-$T_{10}$-tocopherol-3' (SEQ ID NO: 7) |

Synthesis of Small Unilamellar Vesicles

The volume of lipid monomer stock solution (25-50 mg) was added to a 20 mL vial and placed into a 25 mL glass vial and the solvent was carefully evaporated using a stream of nitrogen. The obtained lipid monomer was further dried overnight under vacuum to remove the residual chloroform. The resulting lipid film was then hydrated with 20 mM HBS (5.0 mL) followed by vortexing the vial to form a liposomal suspension. This suspension was further probe-sonicated for 30 min keeping the temperature of the lipid mixture below 10° C. (cooling with an ice-water bath). After the sonication, the suspension was subjected to ultracentrifugation at 100,000×g for 90 min at 12° C. After the centrifugation, the clear supernatant containing the desired small unilamellar vesicles (SUV) was collected and the pellet was discarded (FIG. 1). To obtain particles with a narrower size distribution, the obtained SUV particles were further extruded through polycarbonate membrane (30 nm pore size).

Figure 11:
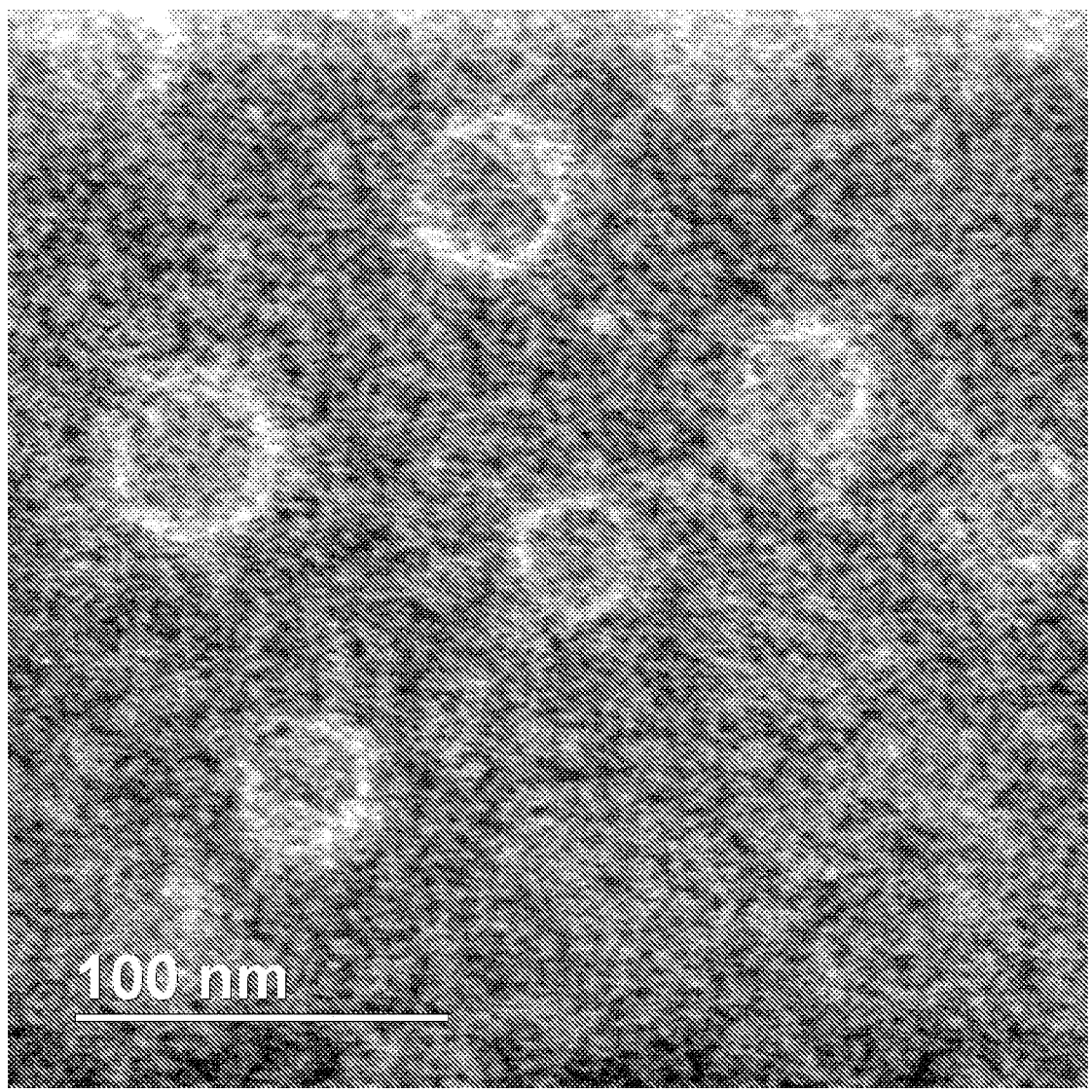
FIG. 11 depicts a TEM micrograph of SUVs after isolation and purification.
Figure 12:
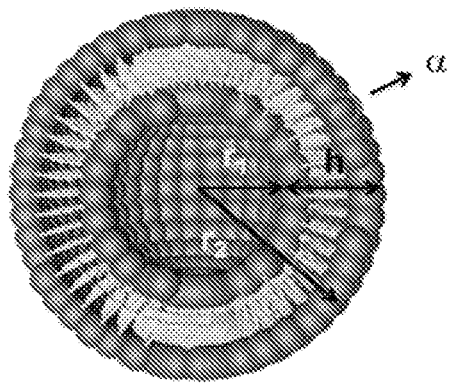
FIG. 12 depicts A) The equation used to calculate the total number of liposomes in a given solution. Concentration of the lipid can be determined using ICP. For most of the studies described herein, working lipid concentration 1.3 mM gives $1.361 \times 10^{17}$ liposomes/L and the DNA loading of 71 DNA strands per particle (4 pmol $cm^2$). B) Particle mobility of liposomal SNAs depending on the estimated oligonucleotide loading.
Figure 12:
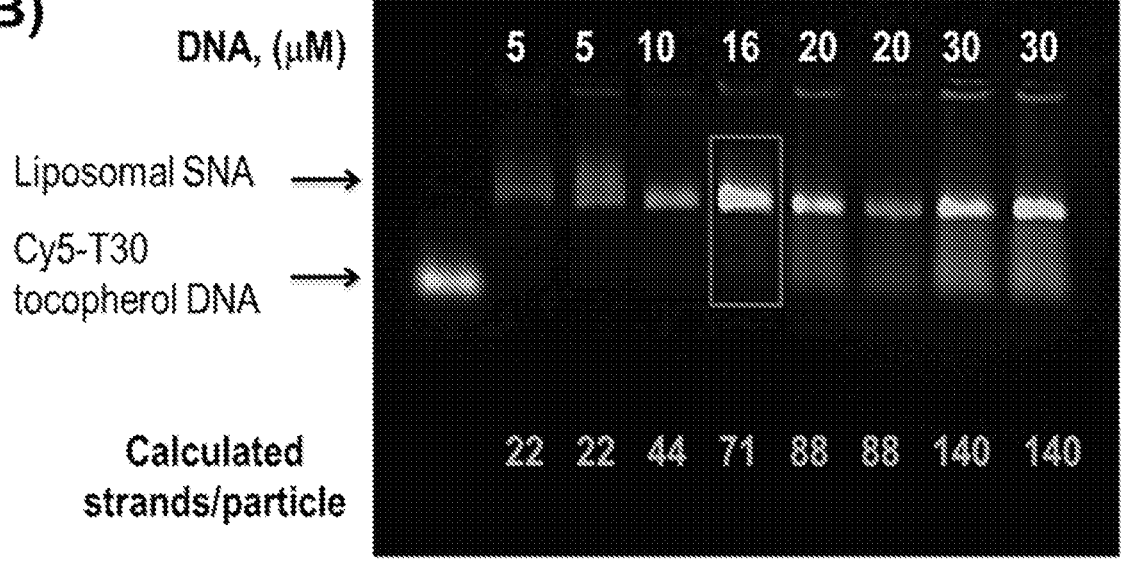

The obtained SUVs were further analyzed using dynamic light scattering (DLS) and transmission electron microscopy (TEM) techniques (FIG. 11). The final phospholipid concentration in a given sample was determined via inductive coupled plasmon mass spectroscopy (ICP-MS). The number of liposomes in solution and the number of oligonucleotides on the surface of a liposome can be calculated according to the equation depicted in FIG. 12.

Preparation of DNA Functionalized Liposomal SNAs

In order to prepare liposomal SNAs, 15 µM of the desired 3'-tocopherol modified oligonucleotide was added to a SUV solution (1.3 mM of [phospholipid]) and allowed to shake overnight. The resulting solution was then purified via gel filtration chromatography on cross-linked sepharose column (Separose CL 4B, Aldrich). The particle size distribution was analyzed using DLS. To observe the liposomal SNAs using TEM, the samples were placed onto plasma-cleaned carbon TEM grids and further stained with solution of uranyl acetate (2% w/v) (stained for 2 min then washed with water and allowed to dry). The dried grid was then imaged under the Hitachi-2300 STEM electron microscope.

Gel Electrophoresis of Liposomal SNAs

All gel electrophoresis experiments were conducted in a 1% agarose gel in 1×TBE (tris borate, EDTA) buffer. The samples were loaded in the wells with the aid of glycerol (30% v/v, 5 µL) as a loading agent. The gel chamber was filled with 1×TBE and was precooled with ice. The gels were run at 70V for 1 hour at 10° C. and the images of the gel were recorded with Fluorchem Q with a Cy5 filter.

Quantification of DNA Density on the Liposomal Surface

To determine the loading of DNA on the surface of liposomes, an increasing concentration of Cy5-labeled 3' tocopherol-modified DNA was incubated overnight with a fixed concentration of SUVs (1.3 mM of [P]). The liposomal SNAs were then analyzed using gel electrophoresis. To quantify the DNA density functionalized on the SUVs, the constructs were dissolved in 1% SDS solution and absorbance was collected at 260 nm and calculated using the extinction coefficient of the respective DNA strand. The number of liposomes in the corresponding solution was calculated using the theoretical equation with the assumption that the phospholipid concentration of the liposomes remains constant after functionalization.

Melting Assays

A two nanoparticle-component system was formed using liposomal SNAs functionalized with strands complementary to the linker strand as described in Table 1. The aggregates were formed by addition of two DNA functionalized Liposomal SNAs and hybridizing them to the linker strand in a 1:1 ratio (the total DNA concentration 1.5 µM, volume 1 mL). The absorbance spectra for the liposomal SNAs with the linker was collected using Cary 5000 UV-Vis spectrometer and compared to the absorbance spectra of liposomal SNAs without the linker. The aggregates were then subjected to a gradual increase in temperature at a rate of 0.25° C./min from 20 to 65° C. and the absorbance was monitored at 260 nm for the aggregates.

Rhodamine Encapsulation

Dry DOPC monomer (25 mg) was resuspended in a 20 mM Sulforhodamine B solution in HBS (5 mL). The resulting suspension was gradually extruded through a series of polycarbonate membranes, 100 nm, 80 nm, 50 nm, 30 nm sizes. The rhodamine containing liposomes were separated from the free rhodamine via gel filtration chromatography on cross-linked sepharose (Sepharose CL-4B, Aldrich). The obtained particles were functionalized with DNA-tocopherol conjugates using the procedure described above. To analyze the serum stability of the constructs, the rhodamine containing liposomes and liposomal-SNAs were suspended in 10% fetal bovine serum solution in HBS, and the release of the dye was monitored in a Fluorlog-3 system by exciting the sample at 420 nm and measuring the intensity at 480 nm.

Cell Culture Studies

SKOV-3 cells were purchased from American Type Culture Collection (ATCC) and were grown in the McCoy's 5A medium with 10% heat inactivated fetal bovine serum, 100 U of penicillin and 50 µg of streptomycin and maintained at 37° C. with 5% CO2 as per ATCC instructions. For cellular studies, the cells were plated 24 hours prior to the treatment at the 50% confluency.

Confocal Microscopy of Liposomal SNAs

For visualizing of the cellular internalization of liposomal SNAs, the SKOV3 cells were plated on 35 mm FluoroDish™ chamber at 50% confluent. The cells were incubated with Cy5-labeled liposomal SNAs (0.1 µM of DNA concentration) in media for 20 hours followed by three washes with 1×PBS containing 0.01% (by volume) tween-20 then replaced with fresh media. The nuclei were stained with Hoechst 3342 (Invitrogen) following the manufacturer's protocol. The live cells were then imaged with Zeiss LSM 510 inverted laser scanning confocal microscope with Mai Tai 3308 laser (Spectra-Physics) at 40× magnification. The Hoechst was excited at 780 nm and collected at 390-495 nm and excited at 640 nm and emission at 650-710 nm.

Flow Cytometry Experiments

To compare the cellular uptake of liposomal SNAs to free-DNA strand, the cells were plated on a 96 well in 100

μL of media and incubated with 0.1 μM concentration of free-DNA or liposomal SNAs and for 24 hours. The untreated cells were used as a negative control for the experiment. After the incubation period, the cells were washed 3 times with 1×PBS containing 0.01% (by volume) of Tween-20 and then trypsinized to form a suspension. Flow cytometry was performed on the cellular suspension using Cy5 intensity channel on Guava easyCyte 8HT (Millipore, USA) using the signal from the untreated cells as for background intensity. The error values were calculated using the standard error of the mean of median signal from different wells representing a single sample.

Cytotoxicity Studies (MTT Assay)

To evaluate the cytotoxicity of the liposomal SNAs, the SKOV-3 cells were plated on a 96 well 24 hours before the experiment. The cells were treated with liposomal SNAs at varying concentration of DNA for 24 hours. The cytotoxicity of liposomal SNAs was compared to DharmaFECT® 1 (Dharmacon), a commercially available transfection agent. The cells were transfected with varying concentrations of DNA transfected with DharmaFECT® 1 following the manufacturer's transfection protocol. The cells, that didn't receive the treatment, were used as a negative control. After the incubation period of 24 hours, the cells were washed three times with 1×PBS and incubated with alamarBlue® solution (Thermo Fisher Scientific Inc.) and incubated at 37° C. in 5% CO2 for 4 hours. The fluorescence emission at 590 nm was recorded using the BioTek, Synergy H4 Hybrid Reader.

Western Blotting to Quantify HER2 Protein Knockdown

The SKOV-3 cells were plated in a 6-well plate and incubated at 37° C. in 5% CO2 overnight. The cells were incubated with anti-HER2 antisense liposomal SNAs and scrambled liposomal SNAs. After a treatment of 24 hours, the medium was replaced with fresh medium and the cells were allowed to grow for an additional 48 hours. To analyze the HER2 protein knockdown, the cells were collected and re-suspended in 100 μL of mammalian cell lysis buffer (Cell Signaling, MA, USA) containing protease and phosphatase inhibitors. (Thermo Scientific, IL, USA). The protein concentration in the cell lysates was determined using a BCA Protein Assay Kit (Pierce, IL, USA). Equal amounts (20 μg) of proteins were fractionated by 4-20% Precast gradient gel (Bio-Rad) and transferred to a nitrocellulose membranes (Thermo Scientific, IL, USA). The membrane was blocked using 5% dry non-fat milk solution (w/v) in tris-buffered saline (TBS). The proteins were detected with primary rabbit antibodies against HER2 (1:1000), and GAPDH (1:500) followed by anti-rabbit secondary antibodies (1:10,000) (LI-COR Biosciences, NE, USA). The fluorescence signal was recorded using the Odyssey® Infrared Imaging System (LI-COR Biosciences, NE, USA).

Synthesis

Figure 7:
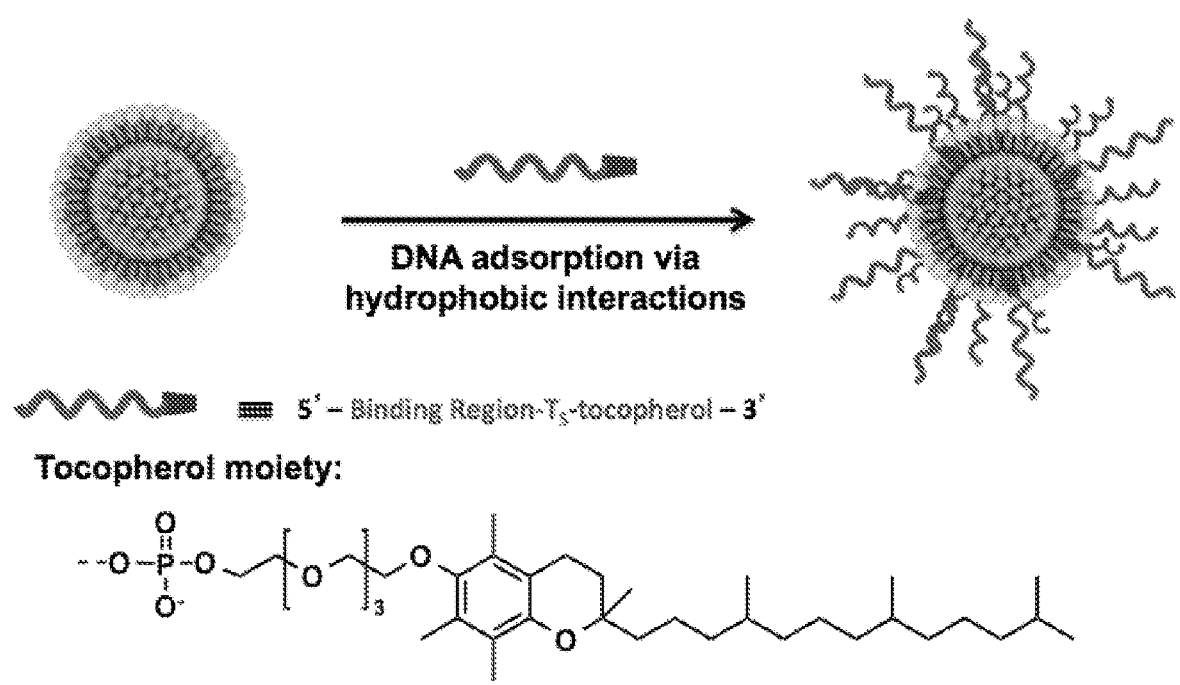
FIG. 7 depicts assembly of liposomal-spherical nucleic acids (SNAs) from a DOPC SUV and tocopherol-modified DNA.

A typical liposomal SNA was synthesized in two steps (FIG. 7). The first step involves the preparation of 30 nm diameter unilamellar vesicles from lipid monomers. This size particle is ideal from the standpoints of SNA transfection and is in the appropriate range for maximizing higher blood circulation and minimizing clearance through the kidneys. Unfortunately, liposomes in this size regime are often unstable and fuse to form larger structures. Therefore, a goal of this work was to determine a way of synthesizing such structures and avoiding such particle growth pathways.

To prepare small unilamellar vesicles (SUVs), DOPC (1,2-dioleoyl-sn-glycero-3-phosphocholine), an unsaturated lipid containing two oleic acid derivatives extending from a phosphate moiety and terminated with a quaternary ammonium head group, was selected. In a typical experiment, a suspension of DOPC monomers in 20 mM HBS was sonicated to produce on average 30 nm SUV particles. The particles were isolated by centrifugation (100,000×g). Further extrusion of this material, through a polycarbonate membrane with 30 nm pores yielded particles with a polydispersity index (PDI) of 0.11 in 70% overall yield. The particles were then redispersed in saline, and DLS was used to confirm their 30±3 nm diameter, which was also subsequently confirmed by TEM analysis using negative staining.

Figure 16:
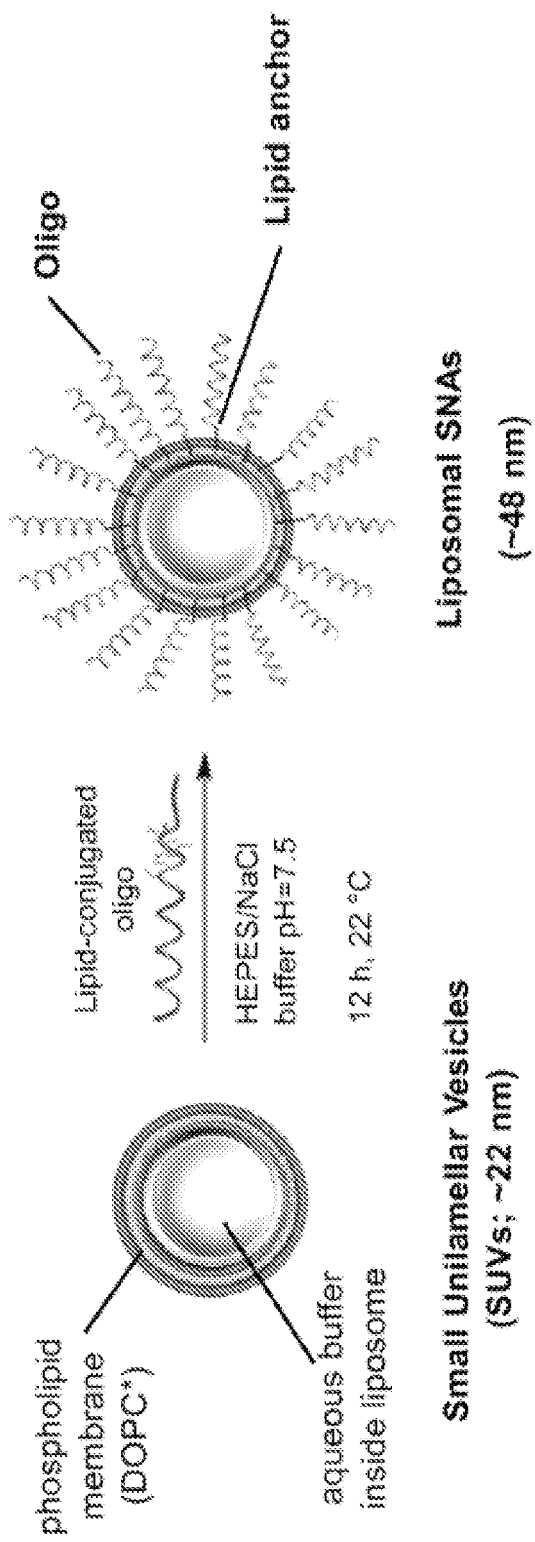
FIG. 16 is a graphical depiction of the synthesis of a liposomal SNA.
Figure 17:
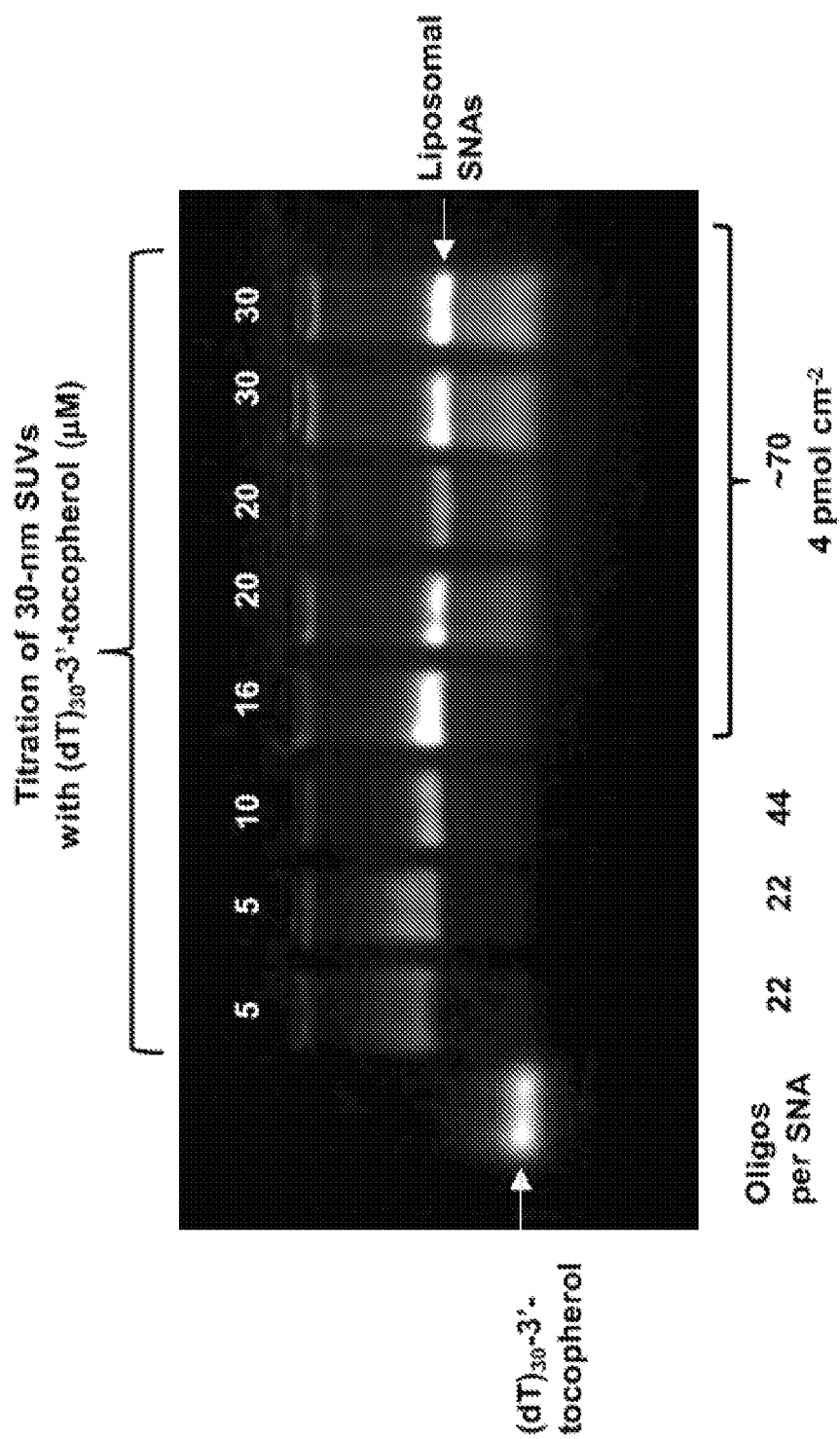
FIG. 17 shows a gel electrophoresis image of liposomal SNAs that were surface functionalized with varying numbers of oligonucleotides. The concentration of 30 nm SUVs was 0.22 µM (determined by analysis of phospholipid content by elemental analysis and approximation of $2.2 \times 10^3$ phospholipids per 30 nm SUV).

The second step of the synthesis involves surface functionalization of the liposome with a nucleic acid derivative possessing a hydrophobic tocopherol moiety, which effectively inserts into the lipid bilayer defining the SUV. Although a variety of hydrophobic head groups might be suitable [Pfeiffer et al., J. Am. Chem. Soc. 126: 10224 (2004); Banchelli et al., J. Phys. Chem. B 112: 10942 (2008); Dave et al., ACS Nano 5: 1304 (2011); Jakobsen et al., Bioconjugate Chem. 24: 1485 (2013)], α-tocopherol (a form of vitamin E) was chosen because of its biocompatibility and low cost. The α-tocopherol was installed onto nucleic acid strands (DNA) via a conventional oligonucleotide synthesis, utilizing a commercially available tocopherol phosphoramidite derivative (Glenn Research). The liposomal SNAs were synthesized by incubating a suspension of SUVs (1.3 mM by lipid) with the nucleic acid-tocopherol conjugates (16 mM) using a lipid-to-nucleic acid ratio of 8:1 for 12 hours at room temperature. The liposome-free tocopherol-nucleic acid was then removed from the sample by size exclusion chromatography on a sepharose column (Sepharose 4LB). In the case of DNA, a significant drop in the zeta potential from −1 to −23 occurs after this step, indicating liposome surface functionalization with the negatively charged nucleic acid. In addition, dynamic light scattering (DLS) analysis of the final nanoparticle samples showed an increase in particle size from 30 to 46 nm, consistent with the loading of the 8-9 nm long duplex structure. To determine quantitatively the average number of nucleic acids loaded onto the surface of a liposome, the liposomal-SNAs were dissolved in the presence of Triton X to release them. The final nucleic acid concentration was determined by measuring the absorbance at 260 nm relative to a calibrated oligonucleotide standard. The liposomal SNAs coated with DNA had on average of 70 strands per particle (FIG. 17). This density is lower than a typical gold-based SNA structure [Hurst et al., Anal. Chem. 78:8313 (2006)] but sufficient to exhibit many of the cooperative properties of such structures. A graphical depiction of a liposomal SNA is provided in FIG. 16.

Figure 2:
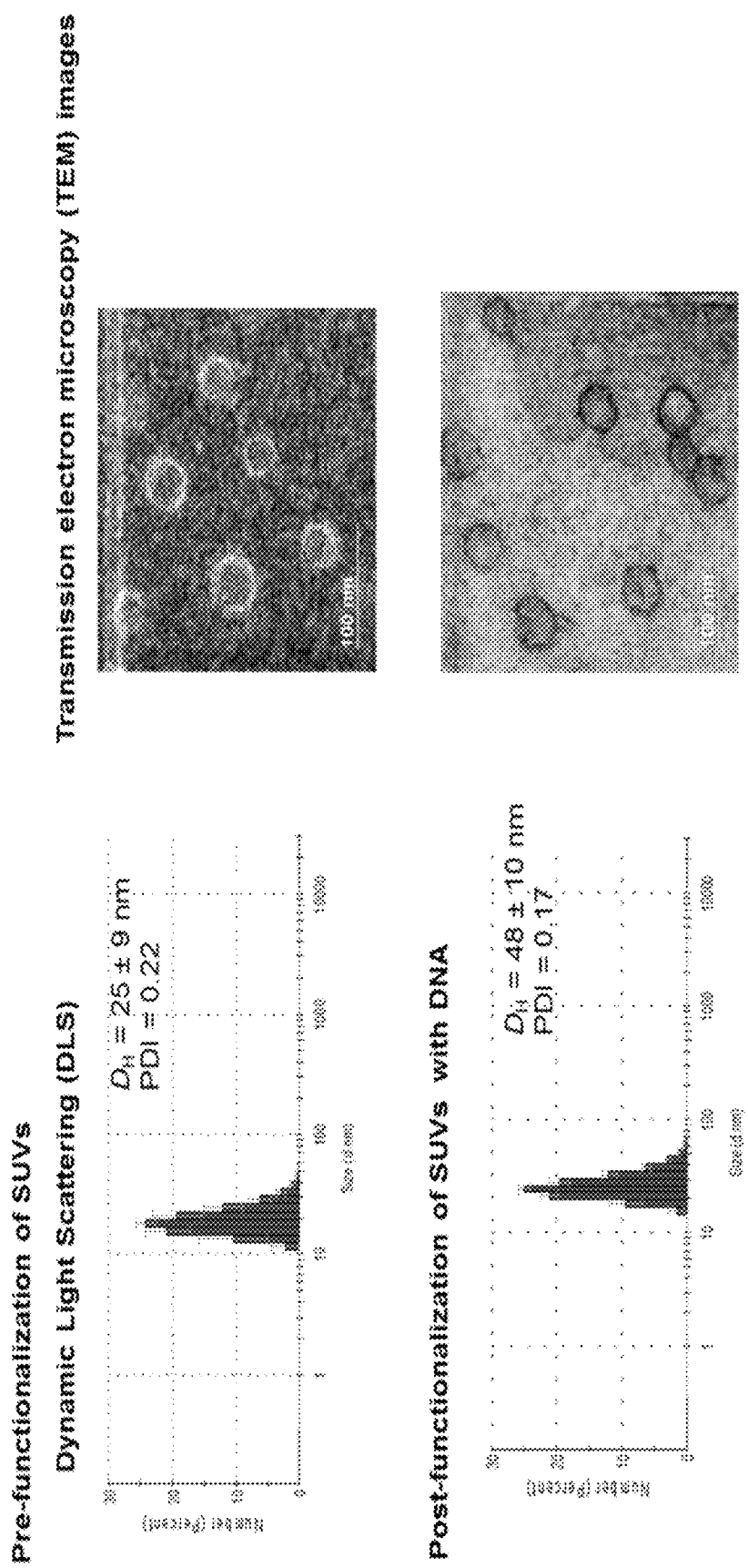
FIG. 2 demonstrates the characterization of liposomal particles from small unilamellar vesicles (SUVs). The dynamic light scattering (DLS) particle size data and transmission electron microscopy (TEM) pictures were obtained before and after functionalization.
Figure 3:
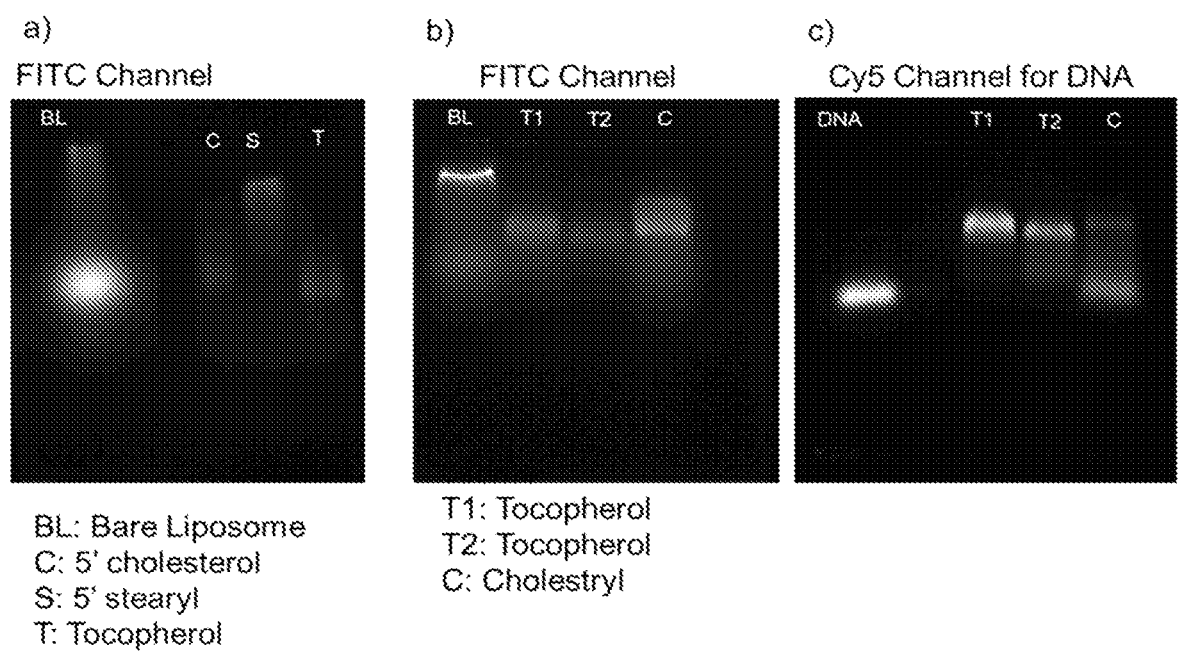
FIG. 3 demonstrates the stability of liposomal particles stabilized with oligonucleotides having different lipophilic ends to anchor the oligonucleotide to the liposome. Liposomes stabilized with tocopherol-modified oligonucleotides demonstrate better stability over bare liposomes, liposomes stabilized with cholesterol-modified oligonucleotides, and liposomes stabilized with stearyl-modified oligonucleotides. a) A gel electrophoresis image of FITC-encapsulated SUVs that have been functionalized with oligonucleotides having different lipophilic ends; b) and c) Gel electrophoresis images of FITC-encapsulated SUVs that have been functionalized with Cy5-labeled DNA.
Figure 4:
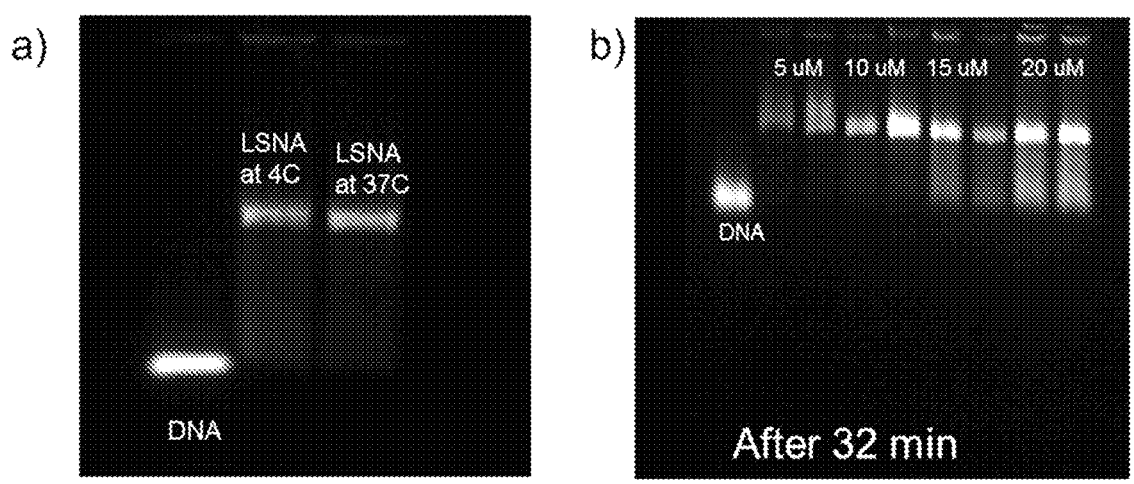
FIG. 4 demonstrates that liposomal particles that have been stabilized with oligonucleotides have good temperature stability and show the range of tocopherol-modified DNA concentrations that were used to stabilize SUVs. a) Stability of the liposomal SNA (LSNAs) after being stored at 37° C. for 24 hours comparing to LSNAs that have been stored at 4° C. b) Gel electrophoresis showing the range of α-tocopherol modified DNA concentrations that were used to stabilize the SUVs.
Figure 8:
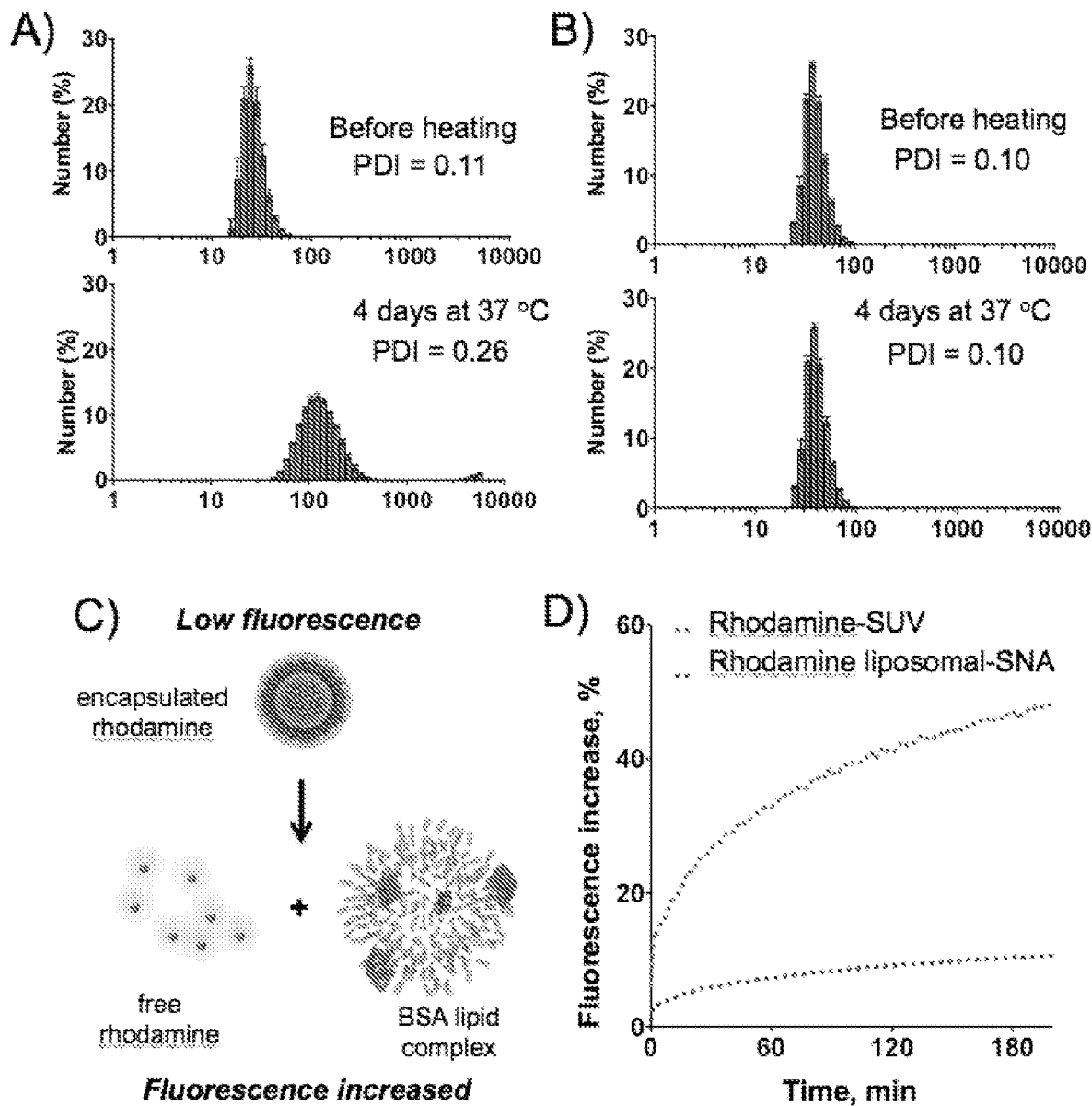
FIG. 8 depicts stability studies of SUVs and LSNAs. (A) Dynamic light scattering profile of SUVs after heating in buffer. (B) Dynamic light scattering profile of LSNA after heating in buffer. (C) Schematic representation of liposome decomposition in the presence of bovine serum albumin, a major component of fetal bovine serum. (D) Degradation of SUVs (upper trace) and LSNAs (lower trace) in the presence 10% fetal bovine serum, as monitored by the release of encapsulated rhodamine dye, which cause in increase in the fluorescence of the solution.

These liposome SNA structures have several interesting properties. First, they are remarkably stable compared to the native 30 nm liposome constructs from which they have been derived (FIG. 2, FIG. 8). For example, if the SUVs without an oligonucleotide surface layer are stored for four days at 37° C. (physiological temperature), they fuse and form larger polydisperse structures (on average 100 nm structures with some micron-sized entities). In contrast, the liposomal SNAs show no evidence of particle degradation or fusion over the same time period under nearly identical conditions. This increase in stability for the liposomal-SNA system is likely a result of the repulsive forces between the negatively charged nucleic acid strands that comprise the liposomal-SNAs surface, which both stabilizes the individual particles and inhibit particle-particle fusion interactions [Li et al., Bioconjugate Chem. 24: 1790 (2013)]. Moreover, the negatively charged DNA corona on the liposomal-SNA serves as a protecting layer for the liposomal core preventing its degradation in the presence of serum proteins [Senior et al., Life Sci. 30: 2123 (1982); Kim et al., Arch. Pharmacal Res. 14: 336 (1991); Sulkowski et al., J. Mol. Struct. 744-747: 737 (2005)]. For example, serum stability of the liposomal-SNAs system was investigated by measuring the release of a sulforhodamine dye physically incorporated within the core of a liposomal-SNA at a self-quenching concentration of 20 mM (core concentration). In this experiment, rupture of the liposomal core results in a release of the sulforhodamine dye from the interior of the particle and a subsequent elimination of self-quenching, thus giving rise to an increase in fluorescence [Versluis et al., J. Am. Chem. Soc. 135: 8057 (2013)]. In a typical experiment, rhodamine-containing liposomal nanoparticles were incubated in 10% fetal bovine serum at 37° C., and the fluorescence spectra were recorded continuously for 3 hours. The same stability study was performed for non-functionalized particles. Similar to the thermal stability studies, DNA-functionalized particles remained stable in serum for the duration of experiment. No release of the dye was observed during 3 hours of incubation. In contrast, incubation of the bare DOPC liposomes led to a significant release of the rhodamine fluorophore indicating fast decomposition of the liposomal structure in serum (FIG. 8).

Figure 9:
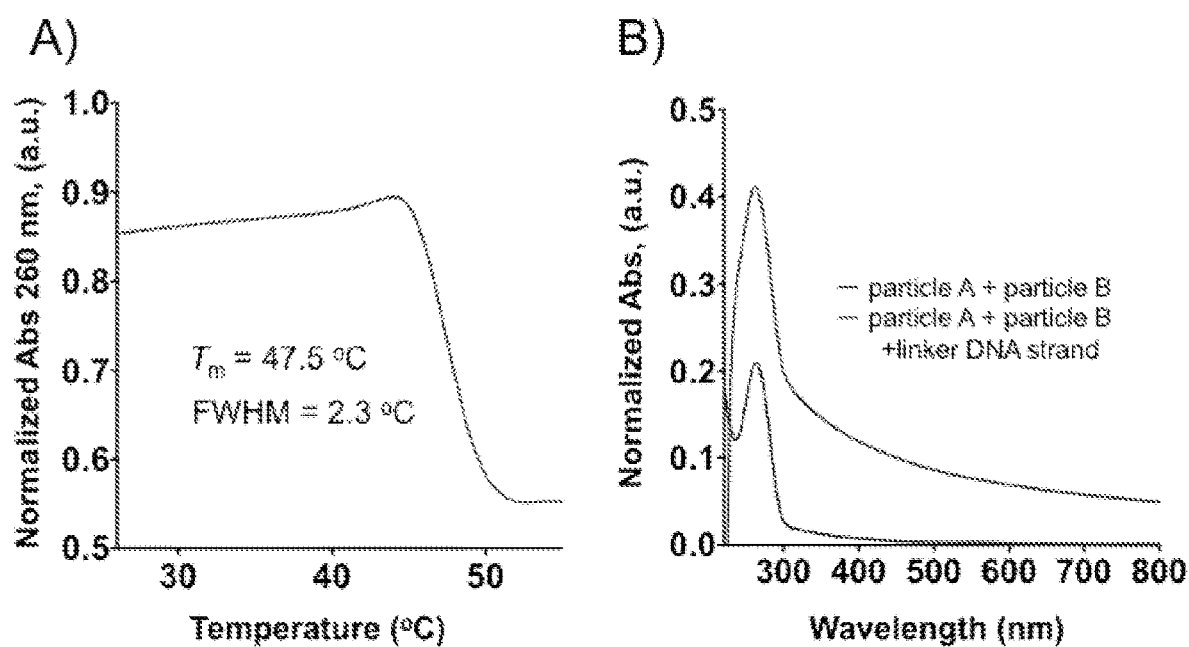
FIG. 9 shows (A) Melting transition of liposomal-SNA aggregates monitored as absorbance at 260 nm. (B) Absorbance spectra of liposomal-SNAs before aggregation (lower trace) and after aggregation in the presence of linker DNA strand (upper trace).

A second property of liposomal SNAs is their ability to cooperatively bind complementary nucleic acids. This is a hallmark feature of all SNAs and derives from the densely packed and highly oriented configuration of the surface-bound nucleic acids. To explore the binding and subsequent melting properties of the liposomal-SNA constructs, two sets of liposomal-SNA nanoparticles were synthesized, each made with different DNA sequences: particle A and particle B. A DNA linker sequence that is complementary to the oligonucleotide sequences of the liposomal-SNAs was used to facilitate polymerization through hybridization. Upon addition of the linker sequence to an equimolar mixture of the two liposomal SNA particles, aggregation occurred as evidenced by DLS and eventually a flaky precipitate was formed [Dave et al., ACS Nano 5: 1304 (2011)]. These aggregates were re-suspended in 20 mM HBS (150 mM NaCl), and a melting analysis was performed by monitoring the absorbance at 260 nm. Importantly, a remarkably narrow melting transition was observed at 47.5° C. (full width at half-maximum of the first derivative is approximately 2° C.), which is highly diagnostic of an SNA structure with a high surface density of nucleic acids (FIG. 9).

Figure 10:
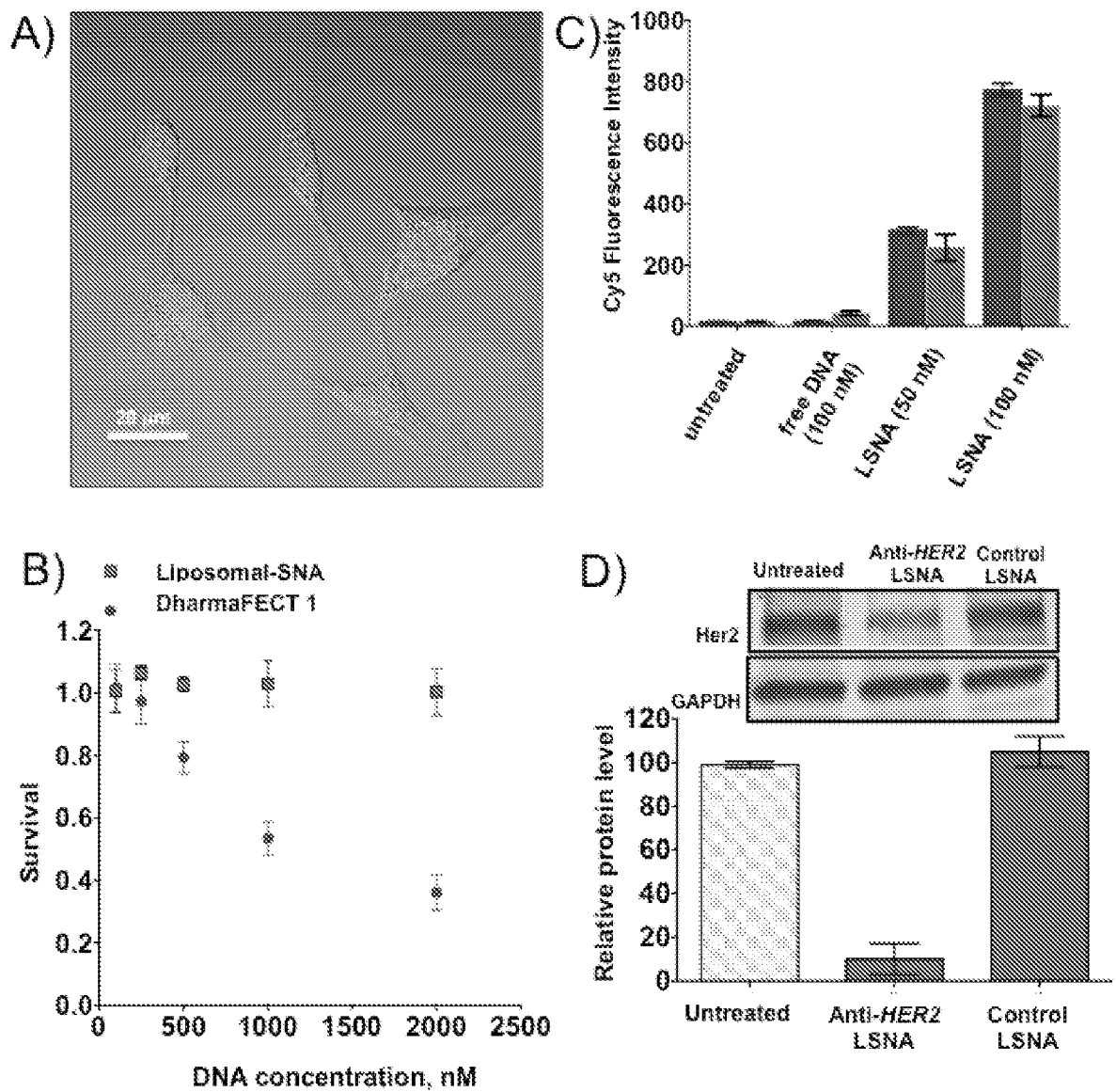
FIG. 10 shows (A) Confocal micrograph of SKOV3 cells incubated with 100 nM Cy5-labelled liposomal-SNAs for 24 hours. Cell nuclei are stained with Hoechst 33342. (B) Cytotoxicity measurements of liposomal-SNAs and DharmaFECT-DNA complex in SKOV3 cells by MTT assay. (C) Cell uptake of 5-Cy5-labelled DNA strand and 5'-Cy5-labelled liposomal-SNAs in SKOV3 cells quantified by flow cytometry after a 1 hour (left bar in each group) and 36 hours (right bar in each group) of incubation. (D) HER2 gene knockdown in SKOV3 cells using anti-HER2 liposomal-SNA constructs at 1 µM DNA concentration.

An important property of SNAs pertains to their ability to enter cells without the need for ancillary transfection agents [Cutler et al., J. Am. Chem. Soc. 134: 1376 (2012)]. To determine if liposomal SNAs exhibit this behavior, ovarian cancer ascites (SKOV3, American Type Culture Collection) were incubated in the presence of the liposomal SNAs synthesized with a 5'-Cy5-labeled DNA in the absence of any transfection agents at different DNA concentrations. The uptake of liposomal-SNAs in SKOV3 cells was analyzed using confocal microscopy and flow cytometry techniques. Remarkably, liposomal SNAs readily entered cells in high quantities even after 1 hour of incubation, which demonstrates their utility as intracellular probes and target regulating agents. In addition, no significant uptake of free DNA strand (5'-Cy5-labeled) in SKOV3 cells was detected even after 36 hours of incubation under identical conditions. Similar to the Au—SNAs, high uptake of liposomal-SNAs in SKOV3 cells didn't cause any toxicity even at high concentrations (FIG. 10). Conversely, employment of the DharmaFECT in an attempt to deliver equal DNA delivered by the liposomal-SNAs resulted in a significant cytotoxicity, which reduced cell viability to 35% over a 24 hour time period of incubation.

After establishing that liposomal-SNAs are not cytotoxic, a liposomal-SNA was synthesized that was capable of knocking down human epidermal growth factor receptor 2 (HER2)—an oncogene overexpressed in SKOV3 cells [Zhang et al., J. Am. Chem. Soc. 134: 16488 (2012)]. To compare the effectiveness of the antisense activity of liposomal-SNAs to that of conventional transfection systems, SKOV3 cells were incubated in the presence of anti-HER2 liposomal-SNAs, and control liposomal-SNAs (each at a total DNA concentration of 1 µM). After 72 hours of incubation, the cells were harvested and analyzed for protein content by Western blotting. Importantly, HER2 protein levels were reduced by 85% in the presence of anti-HER2 liposomal-SNAs compared to the internal reference gene glyceraldehyde 3-phosphate dehydrogenase (GAPDH) (FIG. 10). Collectively, these results demonstrate the potential to use the liposomal-SNAs to effect both cellular transfection and gene regulation.

In summary, a scalable synthetic route for novel metal-free liposomal SNAs has been developed. Such structures are assembled rapidly from readily available, non-toxic starting materials. The nucleic acid architecture not only stabilizes these small liposomal structures but also facilitates their internalization by SKOV3 cells. Consequently, such structures show utility as new biocompatible gene regulation constructs that exhibit many of the attractive properties of the more conventional gold nanoparticle-based SNAs.

Example 6—Testing Liposomal Particles in Ramos-Blue™ Cells

Figure 14:
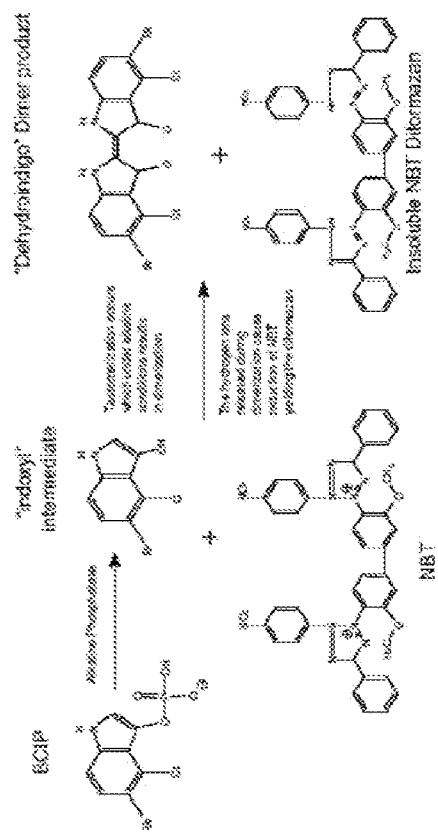
FIG. 14 depicts the Ramos-Blue™ NF-κB/AP-1 reporter system.
Figure 14:
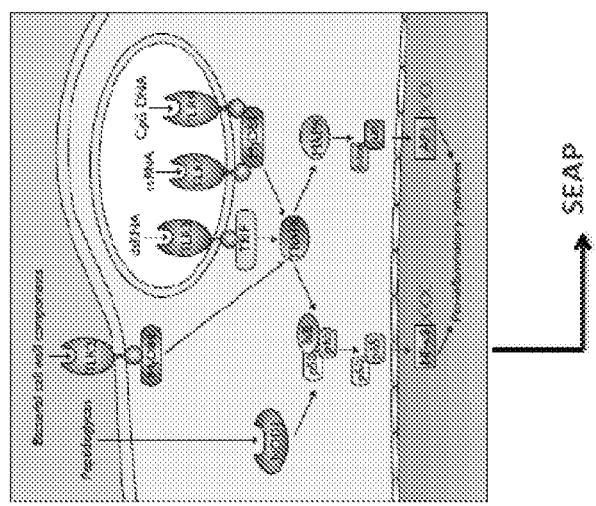

Ramos-Blue™ cells are NF-κB/AP-1 reporter B lymphocyte cells. Ramos-Blue is a B lymphocyte cell line that stably expresses an NF-κB/AP-1-inducible SEAP (secreted embryonic alkaline phosphatase) reporter gene. When stimulated, they produce SEAP in the supernatant that can be readily monitored using the QUANTI-Blue assay. QUANTI-Blue is a SEAP detection medium that turns blue in the presence of SEAP (FIG. 14).

Figure 15:
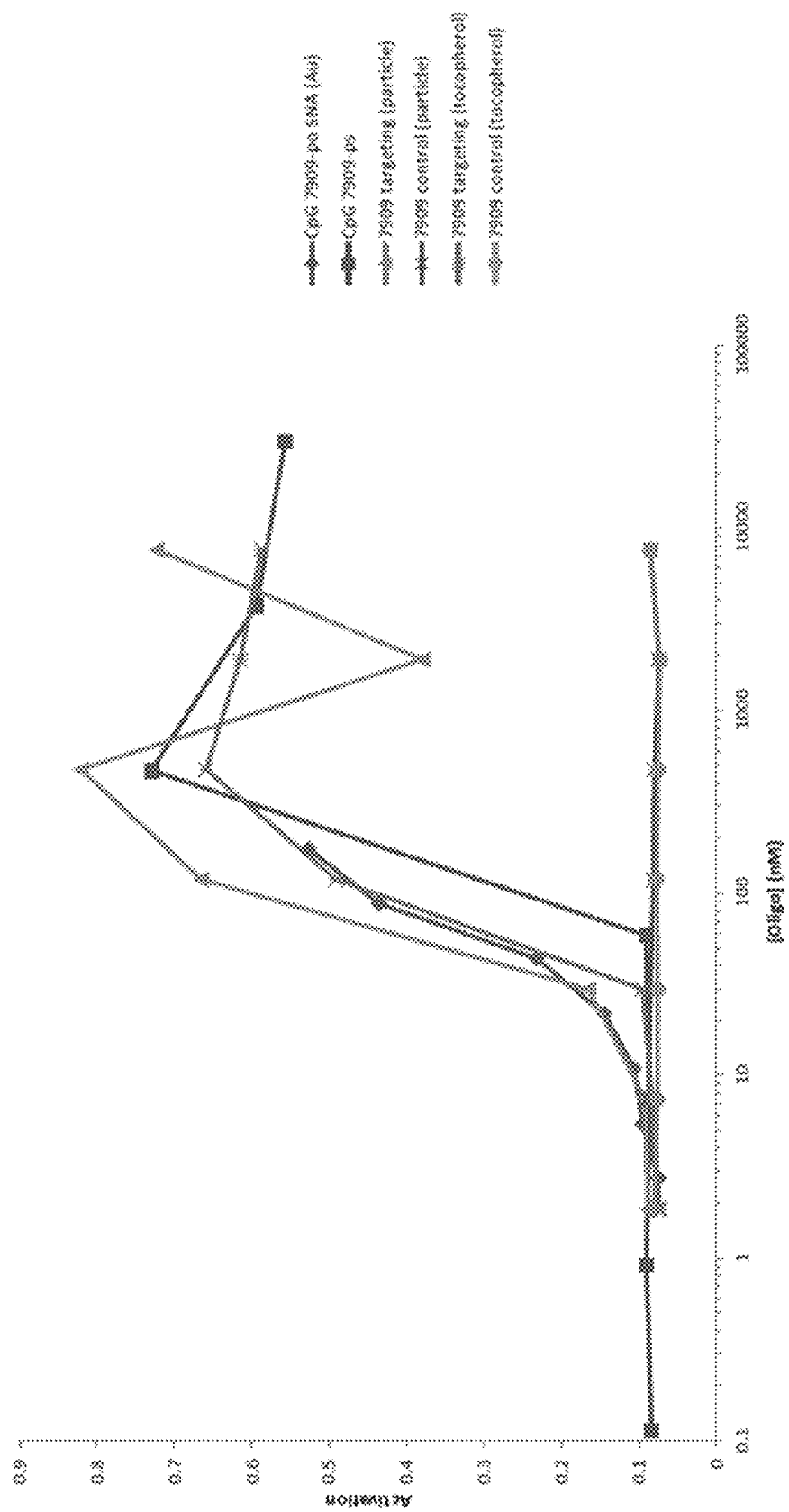
FIG. 15 shows the activation of Ramos-Blue cells when exposed to CpG-containing oligonucleotides.

When contacted with CpG-containing oligonucleotides, activation of the Ramos-Blue cells was detected (FIG. 15). Representative compounds were synthesized based on the TLR 9-agonizing oligonucleotide CpG 7909 (5'-TCGTCGTTTTGTCGTTTTGTCGTT-3' (SEQ ID NO: 8)). These include CpG 7909 with a phosphodiester backbone densely functionalized on 13 nm gold nanoparticles (CpG 7909-po SNA (Au)), CpG 7909 with a fully phosphorothioate backbone (CpG 7909-ps), a liposomal SNA with a phosphodiester CpG 7909 (7909 targeting (particle)), a liposomal SNA with the C and G of the all phosphodiester backbone oligonucleotide inverted to eliminate the TLR 9 binding site (7909 control (particle)), CpG 7909 with a phosphodiester backbone and 3'-tocopherol lipid without being formulated into a liposomal SNA (7909 targeting (tocopherol)), and a control sequence with the C and G inverted that is also not formulated into a liposomal SNA (7909 control (tocopherol)). These compounds were serially diluted then incubated with Ramos-Blue cells, a cell line that expresses secreted alkaline phosphatase (SEAP) upon activation of the pro-inflammatory transcription factor NF-κB, overnight and then probed for SEAP levels in the cell culture media via the QuantiBlue kit (InVivogen). Activation is measured by absorption of light at 650 nm.

Example 7—Use of Liposomal Particles to Regulate HIF1-α

To further demonstrate the effectiveness of a composition of the disclosure, liposomal particles were designed to individually target HIF1-α and BAX. The experiments utilized the Neuro-2a (N2A) cell line, which is a fast-growing mouse neuroblastoma cell line. Contacting the N2A cells with liposomal particles targeting both HIF1-α (FIG. 18) and BAX (FIG. 19) showed a significant reduction in the amount of target gene product. In each of the experiments, the relative amount of mRNA expression was determined by quantitative PCR (qPCR) 72 hours after beginning treatment of the N2A cells in 6-well plates—cells were treated with the liposomal particles for 24 hours in OptiMEM prior to removal of the liposomal particles and replacement of the media with MEM and 10% fetal bovine serum (FBS).

Figure 18:
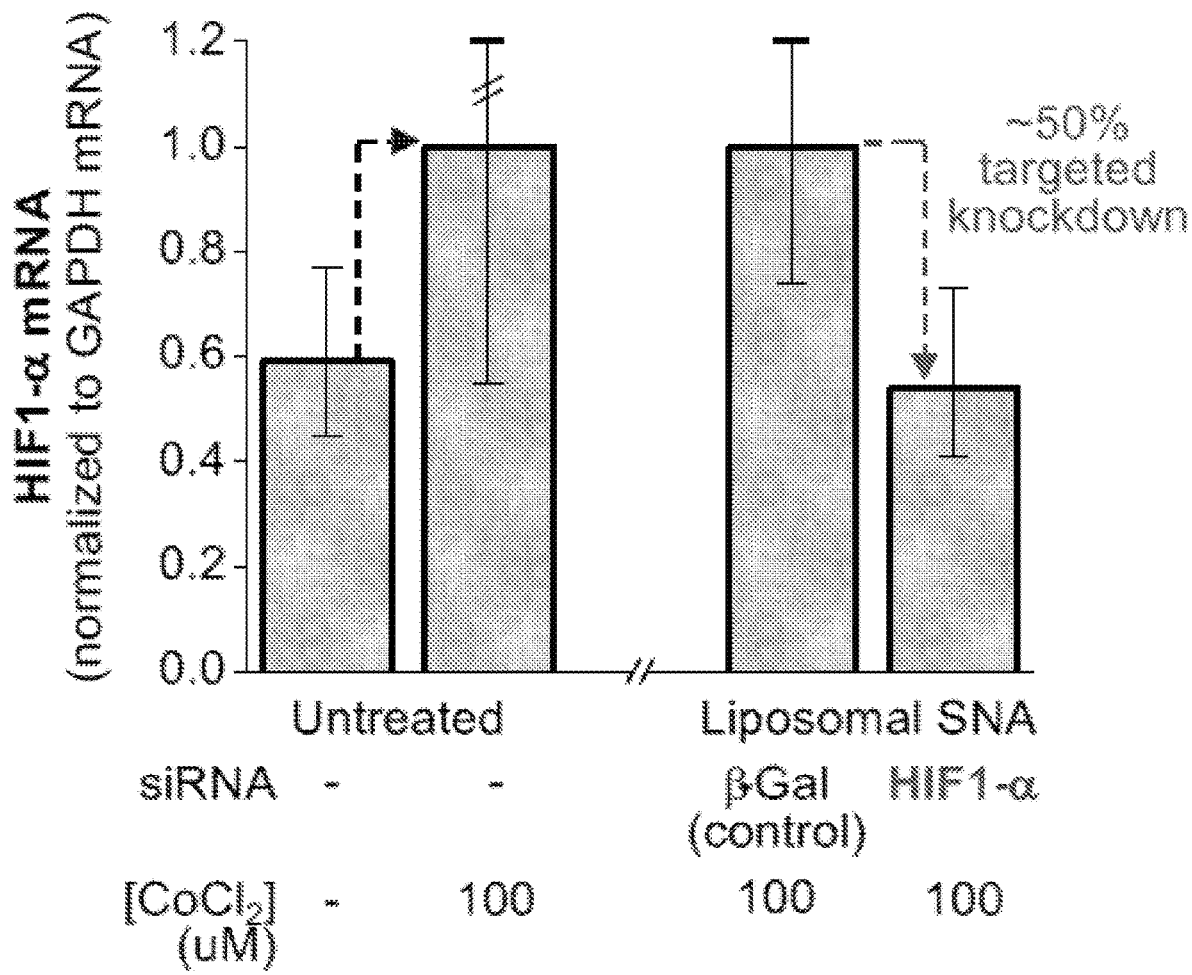
FIG. 18 shows the results of experiments in which liposomal particles were used to knock down the expression of HIF1-α.

For the experiments in which HIF1-α was targeted, the N2A cells were first subjected to Cocl2-stimulated hypoxia, which increased HIF1-α mRNA expression by about 50%. Next, the N2A cells were contacted with the liposomal particles functionalized with siRNA directed against HIF1-α. The contacting resulted in a knockdown of HIF1-α of about 50% (FIG. 18).

Figure 19:
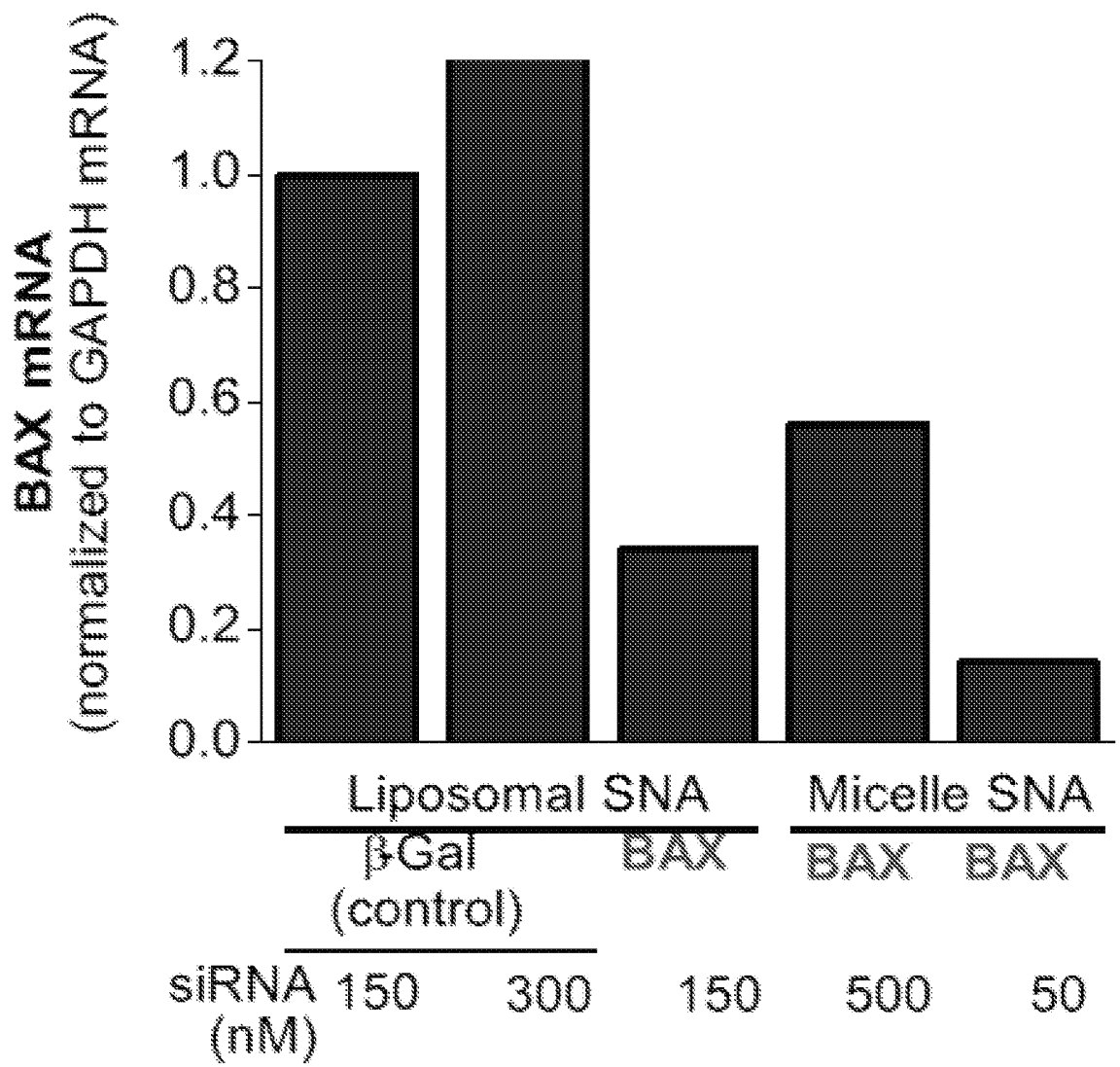
FIG. 19 shows the results of experiments in which liposomal particles were used to knock down the expression of BAX.

For the experiments in which BAX was targeted, treatment of N2A cells with the resulted in an approximate 65% knockdown of BAX mRNA by the liposomal particles and greater than 50% knockdown of BAX mRNA by lipid micelle SNAs (as measured against control liposomal SNAs) (FIG. 19).

These experiments showed that the liposomal particles of the disclosure are highly effective at inhibiting target gene expression in mammalian cells.

It will be evident to one skilled in the art that the present invention is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims and therefore intended to be embraced therein.

What is claimed is:

1. A liposomal particle having a substantially spherical geometry, comprising:
a lipid bilayer comprising a plurality of lipid groups; and single-stranded oligonucleotides that are inhibitory RNA or antisense DNA, wherein all the oligonucleotides are attached to the surface of the liposomal particle, wherein each oligonucleotide is an oligonucleotide-lipid conjugate containing one lipophilic tethered group anchored into the external side of the lipid bilayer, wherein one or more of the oligonucleotides hybridize to a gene comprising a polynucleotide encoding a gene product and are complementary to all or a portion of the polynucleotide, wherein the hybridizing between the oligonucleotide and the polynucleotide occurs over a length of the polynucleotide with a degree of complementarity sufficient to inhibit expression of the gene product, and wherein the diameter of the liposomal particle is less than or equal to 50 nanometers (nm).

2. The liposomal particle of claim 1, wherein the plurality of lipid groups comprises a lipid selected from the group consisting of the phosphatidylcholine, phosphatidylglycerol, and phosphatidylethanolamine family of lipids.

3. The liposomal particle of claim 2, wherein the lipid is selected from the group consisting of 1,2-dioleoyl-sn-glycero-3-phosphocholine (DOPC), 1,2-dimyristoyl-sn-phosphatidylcholine (DMPC), 1-palmitoyl-2-oleoyl-sn-phosphatidylcholine (POPC), 1,2-distearoyl-sn-gl ycero-3-phospho-(l'-rac-glycerol) (DSPG), 1,2-dioleoyl-sn-glycero-3-phospho-(l'-rac-glycerol) (DOPG), 1,2-distearoyl-sn-glycero-3-phosphocholine (DSPC), 1,2-dipalmitoyl-sn-glycero-3-phosphocholine (DPPC), 1,2-di-(9Z-octadecenoyl)-sn-glycero-3-phosphoethanolamine (DOPE), and 1,2-dihexadecanoyl-sn-glycero-3-phosphoethanolamine (DPPE).

4. The liposomal particle of claim 1, wherein the lipophilic tethered group comprises a tocopherol or cholesterol.

5. The liposomal particle of claim 4, wherein the tocopherol is chosen from the group consisting of a tocopherol derivative, alpha-tocopherol, beta-tocopherol, gam ma-tocopherol and delta-tocopherol.

6. The liposomal particle of claim 1, wherein the inhibitory RNA is selected from the group consisting of a small inhibitory RNA (siRNA), a miRNA, an inhibitory RNA that forms a triplex with double stranded DNA, and a ribozyme.

7. The liposomal particle of claim 1, wherein the liposomal particle comprises from about 10 to about 80 oligonucleotides.

8. The liposomal particle of claim 7, wherein the particle comprises 70 oligonucleotides.

9. The liposomal particle of claim 7, wherein the liposomal particle comprises 30 oligonucleotides.

10. The liposomal particle of claim 1, wherein the oligonucleotides are modified oligonucleotides having phosphorothioate linkages.

11. The liposomal particle of claim 1, wherein the diameter of the liposomal particle is less than or equal to 40 nanometers (nm).

12. The liposomal particle of claim 1, wherein the diameter of the liposomal particle is less than or equal to 35 nanometers (nm).

13. The liposomal particle of claim 1, wherein the diameter of the liposomal particle is less than or equal to 30 nanometers (nm).

14. The liposomal particle of claim 1, wherein the lipophilic tethered group is at the 3'-end of each oligonucleotide.

15. A plurality of liposomal particles comprising a plurality of the liposomal particle of claim 1, wherein the plurality of liposomal particles has a mean diameter of less than or equal to about 50 nanometers (nm).

16. The plurality of liposomal particles of claim 15, wherein the plurality of liposomal particles has a mean diameter of less than or equal to about 40 nanometers (nm).

17. The plurality of liposomal particles of claim 15, wherein the plurality of liposomal particles has a mean diameter of less than or equal to about 35 nanometers (nm).

18. The plurality of liposomal particles of claim 15, wherein the plurality of liposomal particles has a mean diameter of less than or equal to about 30 nanometers (nm).

19. A liposomal particle having a substantially spherical geometry, consisting of:
a lipid bilayer consisting of a plurality of lipid groups; and single-stranded oligonucleotides that are inhibitory RNA or antisense DNA, wherein all the oligonucleotides are attached to the surface of the liposomal particle, wherein each oligonucleotide is an oligonucleotide-lipid conjugate containing one lipophilic tethered group anchored into the external side of the lipid bilayer, wherein one or more of the oligonucleotides hybridize to a gene comprising a polynucleotide encoding a gene product and are complementary to all or a portion of the polynucleotide, wherein the hybridizing between the polynucleotide and the oligonucleotide occurs over a length of the polynucleotide with a degree of complementarity sufficient to inhibit expression of the gene product, and wherein the diameter of the liposomal particle is less than or equal to 50 nanometers (nm).

20. A plurality of liposomal particles comprising a plurality of the liposomal particle of claim 19, wherein the plurality of liposomal particles has a mean diameter of less than or equal to about 50 nanometers (nm).

21. The plurality of liposomal particles of claim 20, wherein the plurality of liposomal particles has a mean diameter of less than or equal to about 40 nanometers (nm).

22. The plurality of liposomal particles of claim 20, wherein the plurality of liposomal particles has a mean diameter of less than or equal to about 35 nanometers (nm).

23. The plurality of liposomal particles of claim 20, wherein the plurality of liposomal particles has a mean diameter of less than or equal to about 30 nanometers (nm).

* * * * *